US012727787B2

(12) United States Patent
Wang et al.

(10) Patent No.: US 12,727,787 B2
(45) Date of Patent: Sep. 8, 2026

(54) MEASUREMENT DEVICE, MEASUREMENT SYSTEM, MEASUREMENT METHOD, AND RECORDING MEDIUM

(71) Applicant: NEC Corporation, Tokyo (JP)

(72) Inventors: Zhenwei Wang, Tokyo (JP); Chenhui Huang, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 302 days.

(21) Appl. No.: 18/287,549

(22) PCT Filed: Feb. 10, 2022

(86) PCT No.: PCT/JP2022/005234
§ 371 (c)(1),
(2) Date: Oct. 19, 2023

(87) PCT Pub. No.: WO2022/230299
PCT Pub. Date: Nov. 3, 2022

(65) Prior Publication Data
US 2024/0206767 A1 Jun. 27, 2024

(30) Foreign Application Priority Data
Apr. 28, 2021 (JP) ................................ 2021-075661

(51) Int. Cl.
*A61B 5/107* (2006.01)
*A61B 5/00* (2006.01)
(Continued)

(52) U.S. Cl.
CPC .......... *A61B 5/1122* (2013.01); *A61B 5/4571* (2013.01); *A61B 5/4585* (2013.01);
(Continued)

(58) Field of Classification Search
CPC ... A61B 5/1122; A61B 5/4571; A61B 5/4585; A61B 5/4595; A61B 5/742; A61B 5/107;
(Continued)

(56) References Cited

U.S. PATENT DOCUMENTS 10,716,495 B1 * 7/2020 Romrell ................. A61B 5/681
2016/0166880 A1 6/2016 Nakajima
(Continued)

FOREIGN PATENT DOCUMENTS

CN 112043276 A 12/2020
JP S55-134654 U 9/1980
(Continued)

OTHER PUBLICATIONS

JP Office Action for JP Application No. 2023-517071, mailed on Aug. 20, 2024 with English Translation.
(Continued)

*Primary Examiner* — Robert R Raevis
(74) *Attorney, Agent, or Firm* — Sughrue Mion, PLLC

(57) ABSTRACT

A measurement device that includes a calculation unit that calculates, using sensor data measured by a sensor according to a measurement motion regarding a limb of a user, the sensor being attached to the user at a predetermined attachment site, a length and a central angle of an arc related to a trajectory of the sensor in a period of the measurement motion, and an estimation unit that estimates a radius of the arc calculated using the calculated length and the calculated central angle of the arc as a length of the limb of the user.

7 Claims, 26 Drawing Sheets

(51) Int. Cl.
*A61B 5/11* (2006.01)
*G01C 21/16* (2006.01)

(52) U.S. Cl.
CPC ............ *A61B 5/4595* (2013.01); *A61B 5/742* (2013.01); *G01C 21/16* (2013.01)

(58) Field of Classification Search
CPC ... A61B 5/1071; A61B 5/1114; A61B 5/1121; A61B 5/4528; A61B 5/6828; A61B 5/11; G01C 21/16; G01B 21/02

USPC ....................... 73/488, 490, 493, 503–54.17, 73/514.01–514.4, 514.16–514.37, 865.4, 73/865.8; 33/1 PT, 700, 701, 511, 512, 33/534, 548; 702/127, 141, 142, 145, 702/149–153, 155; 600/587, 595
See application file for complete search history.

(56) References Cited

U.S. PATENT DOCUMENTS

2018/0235515 A1 8/2018 Naito et al.
2020/0405185 A1 12/2020 Ohashi

FOREIGN PATENT DOCUMENTS

JP 2010-014712 A 1/2010
JP 2016-112108 A 6/2016
JP 2017-146116 A 8/2017
WO 2017/141565 A1 8/2017
WO 2019/176090 A1 9/2019

OTHER PUBLICATIONS

International Search Report for PCT Application No. PCT/JP2022/005234, mailed on May 10, 2022.
English translation of Written opinion for PCT Application No. PCT/JP2022/005234, mailed on May 10, 2022.

* cited by examiner (1)
(2)
(3)
L
L1
L2
11
11
11
$C_C$
Z
Y
X
Z
Y
X
Z
Y
X

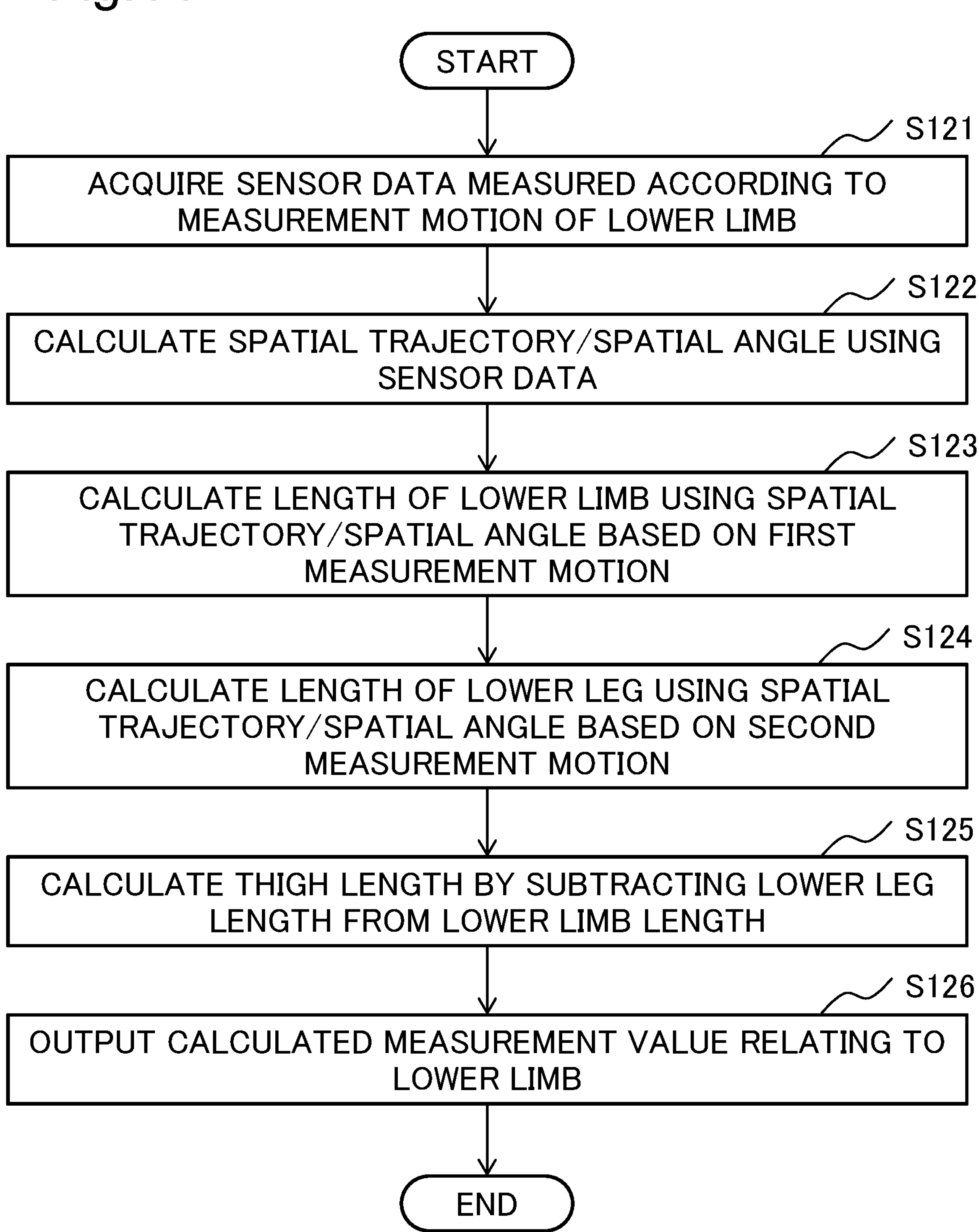
Fig.14
START
S121
ACQUIRE SENSOR DATA MEASURED ACCORDING TO MEASUREMENT MOTION OF LOWER LIMB
S122
CALCULATE SPATIAL TRAJECTORY/SPATIAL ANGLE USING SENSOR DATA
S123
CALCULATE LENGTH OF LOWER LIMB USING SPATIAL TRAJECTORY/SPATIAL ANGLE BASED ON FIRST MEASUREMENT MOTION
S124
CALCULATE LENGTH OF LOWER LEG USING SPATIAL TRAJECTORY/SPATIAL ANGLE BASED ON SECOND MEASUREMENT MOTION
S125
CALCULATE THIGH LENGTH BY SUBTRACTING LOWER LEG LENGTH FROM LOWER LIMB LENGTH
S126
OUTPUT CALCULATED MEASUREMENT VALUE RELATING TO LOWER LIMB
END (1)
(2)
(3)
L
L1
L2
21A
21B
$C_{LA}$
$C_{LB}$

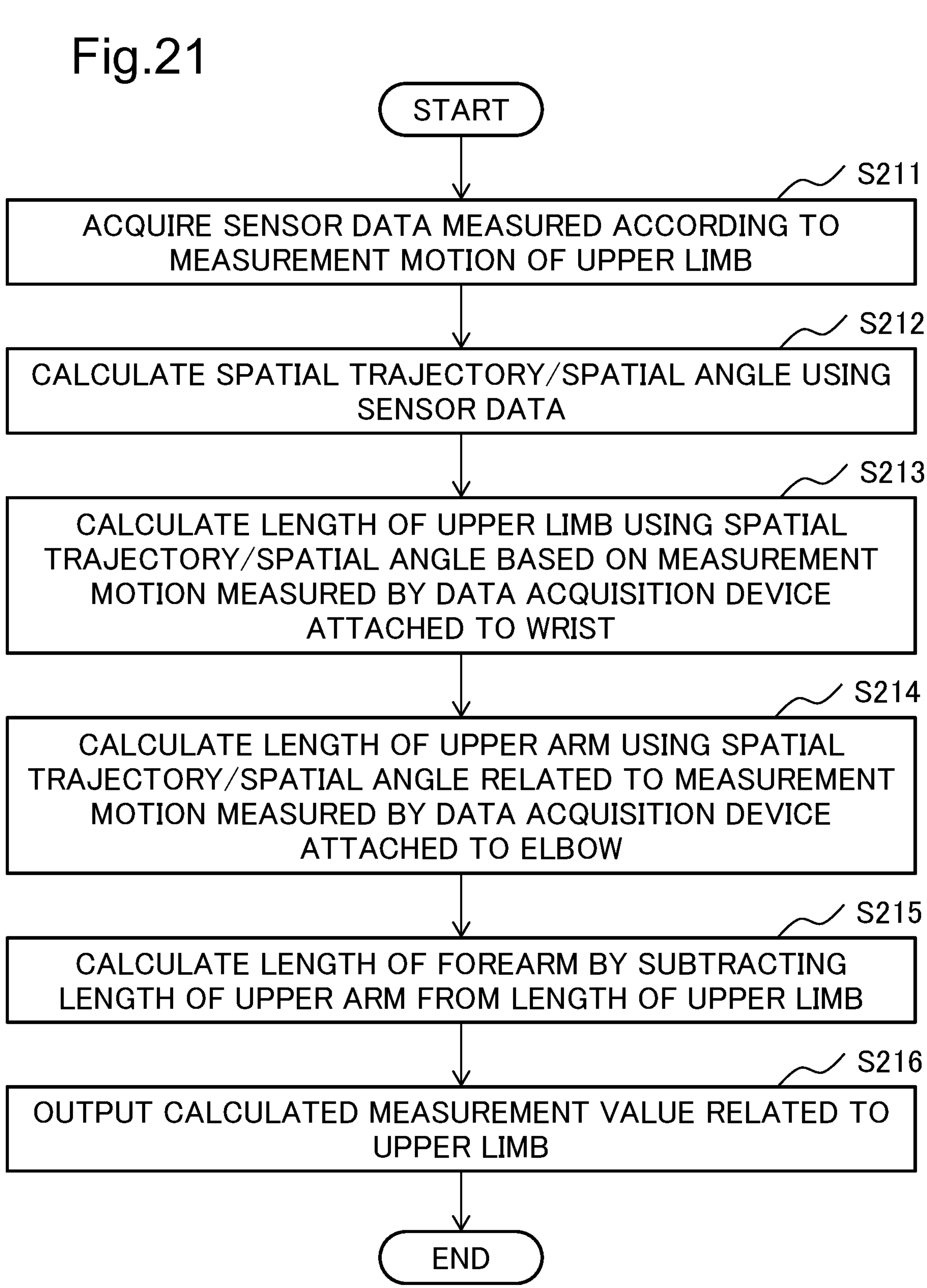
Fig.21
START
S211
ACQUIRE SENSOR DATA MEASURED ACCORDING TO MEASUREMENT MOTION OF UPPER LIMB
S212
CALCULATE SPATIAL TRAJECTORY/SPATIAL ANGLE USING SENSOR DATA
S213
CALCULATE LENGTH OF UPPER LIMB USING SPATIAL TRAJECTORY/SPATIAL ANGLE BASED ON MEASUREMENT MOTION MEASURED BY DATA ACQUISITION DEVICE ATTACHED TO WRIST
S214
CALCULATE LENGTH OF UPPER ARM USING SPATIAL TRAJECTORY/SPATIAL ANGLE RELATED TO MEASUREMENT MOTION MEASURED BY DATA ACQUISITION DEVICE ATTACHED TO ELBOW
S215
CALCULATE LENGTH OF FOREARM BY SUBTRACTING LENGTH OF UPPER ARM FROM LENGTH OF UPPER LIMB
S216
OUTPUT CALCULATED MEASUREMENT VALUE RELATED TO UPPER LIMB
END (1)
PLEASE PERFORM MEASUREMENT MOTION ON UPPER LIMB.
26
21B
21A
21B
21A
(2)
21B
21A
21B
21A
(3)
21B
21A
21B
21A
(4)
PLEASE PERFORM MEASUREMENT MOTION ON LOWER LIMB.
26
21B
21A
21B
21A
(5)
21B
21A
(6)
21B
21A

91 PROCESSOR

92 MAIN STORAGE DEVICE

93 AUXILIARY STORAGE DEVICE

98

95 INPUT/OUTPUT I/F

96 COMMUNICATION I/F

NETWORK

MEASUREMENT DEVICE, MEASUREMENT SYSTEM, MEASUREMENT METHOD, AND RECORDING MEDIUM

This application is a National Stage Entry of PCT/JP2022/005234 filed on Feb. 10, 2022, which claims priority from Japanese Patent Application 2021-075661 filed on Apr. 28, 2021, the contents of all of which are incorporated herein by reference, in their entirety.

TECHNICAL FIELD

The present disclosure relates to a measurement device or the like that performs measurement regarding the limb.

BACKGROUND ART

Due to an increase in interest in healthcare for physical condition management, attention has been focused on simple measurement of a part constituting a body. For example, when the length of the limb can be easily measured, it is possible to set an appropriate exercise program according to the measurement value. In order to accurately measure the length of the limb, specialized knowledge is required. Therefore, it is difficult to easily measure the length of the limb without specialized knowledge.

PTL 1 discloses an exercise state display system that displays a moving image that reproduces a motion state of a human body based on sensor data related to the motion state of the human body measured by a sensor unit attached to an ankle. The system of PTL 1 calculates a parameter that defines at least one of a wearing state of the sensor unit, a single-leg standing posture, and a lower leg length based on sensor data acquired when a calibration motion is performed. The system of PTL 1 generates a moving image that reproduces the motion state of the human body based on the sensor data acquired during the exercise and the value of the parameter calculated by the calibration process.

CITATION LIST

Patent Literature

PTL 1: JP 2016-112108 A

SUMMARY OF INVENTION

Technical Problem

In the method of PTL 1, a series of bending motions is performed during the calibration motion. In a series of bending motions, after the lower leg is moved to a position rotated backward by 90 degrees with the knee as a rotation axis, the lower leg is returned to the initial position where the left leg is upright repeatedly. In the method of PTL 1, it is required that the lower leg be as upright as possible in an upright state. In the method of PTL 1, in order to bend the lower leg with the knee as an axis at the time of the bending motion, it is required that the position of the knee is not moved as much as possible. That is, in the method of PTL 1, it is difficult to accurately measure the parameters related to the body without performing a strict calibration motion.

An object of the present disclosure is to provide a measurement device or the like capable of performing measurement regarding the limb based on sensor data measured according to a simple motion.

Solution to Problem

A measurement device according to an aspect of the present disclosure includes a calculation unit that calculates, using sensor data measured by a sensor according to a measurement motion regarding a limb of a user, the sensor being attached to the user at a predetermined attachment site, a length and a central angle of an arc related to a trajectory of the sensor in a period of the measurement motion, and an estimation unit that estimates a radius of the arc calculated using the calculated length and the calculated central angle of the arc as a length of the limb of the user.

A measurement method according to an aspect of the present disclosure includes calculating, using sensor data measured by a sensor according to a measurement motion regarding a limb of a user, the sensor being attached to the user at a predetermined attachment site, a length and a central angle of an arc related to a trajectory of the sensor in a period of the measurement motion, and estimating a radius of the arc calculated using the calculated length and the calculated central angle of the arc as a length of the limb of the user.

A program according to an aspect of the present disclosure causes a computer to execute calculating, using sensor data measured by a sensor according to a measurement motion regarding a limb of a user, the sensor being attached to the user at a predetermined attachment site, a length and a central angle of an arc related to a trajectory of the sensor in a period of the measurement motion, and estimating a radius of the arc calculated using the calculated length and the calculated central angle of the arc as a length of the limb of the user.

Advantageous Effects of Invention

According to the present disclosure, it is possible to provide a measurement device or the like capable of performing measurement regarding the limb based on sensor data measured according to a simple motion.

BRIEF DESCRIPTION OF DRAWINGS

FIG. 14 is a flowchart for describing an example of measurement of the length of the lower limb by the measurement device of the measurement system according to the first example embodiment.

FIG. 21 is a flowchart for describing an example of measurement of the length of the upper limb by the measurement device of the measurement system according to the second example embodiment.

FIG. 26 is a block diagram illustrating an example of a hardware configuration that implements control and processing of each example embodiment.

EXAMPLE EMBODIMENT

Figure 1:
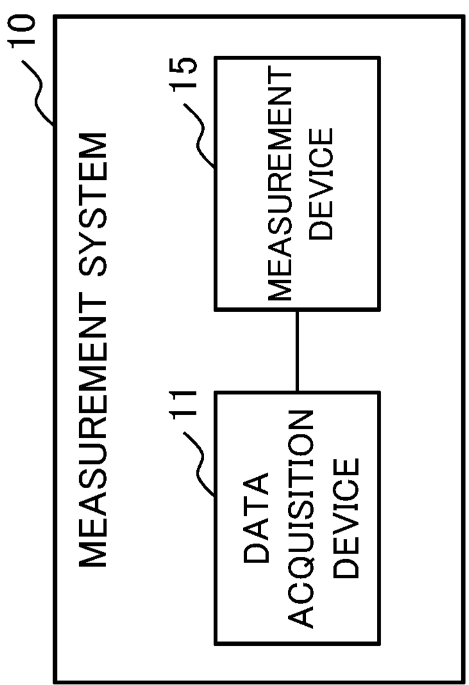
FIG. 1 is a block diagram illustrating an example of a configuration of a measurement system according to a first example embodiment.

Hereinafter, embodiments of the present example invention will be described with reference to the drawings. However, the example embodiments described below have technically preferable limitations for carrying out the present example invention, but the scope of the invention is not limited to the following. In all the drawings used in the following description of the example embodiment, the same reference numerals are given to the same parts unless there is a particular reason. In the following example embodiments, repeated description of similar configurations and operations may be omitted. The directions of the arrows in the drawings illustrate examples of time and a flow of processing, and do not limit the time and the direction of the flow of processing.

In the present disclosure, the name of each part of the human body is defined as follows. The upper limb is a portion between the shoulder joint and the wrist joint. The upper arm is a portion between the shoulder joint and the elbow joint. The forearm is a portion between the elbow joint and the wrist joint. The lower limb is a portion between the hip joint and the ankle joint. The thigh is a portion between the hip joint and the knee joint. The lower leg is a portion between the knee joint and the ankle joint. The shoulder joint and the hip joint are collectively referred to as a large joint. The elbow joint and knee joint are collectively referred to as a middle joint. The wrist joint and the ankle joint are collectively referred to as a small joint. The upper limb and the lower limb are collectively referred to as a limb. The upper arm and the thigh are collectively referred to as "an upper parts of the limb". The forearm and the lower leg are collectively referred to as "a lower parts of the limb". The definition of the name of each joint or each portion in the present disclosure may be different from the medical definition or the kinematic definition.

In the present disclosure, the limb and the like may be expressed by the following rules. The "upper limb or lower limb" is referred to as the "upper limb/lower limb". The "upper arm or thigh" is referred to as the "upper arm/thigh". The "forearm or lower leg" is referred to as the "forearm/lower leg". When other words are written using "/", it is indicated that they are either a word before "/" or a word after "/". For example, in one paragraph or sentence, "upper limb/lower limb", "upper arm/thigh", "forearm/lower leg", and the like may be used in combination. In such a case, it means combining words before "/" and combining words after "/".

First Example Embodiment

First, a measurement system according to a first example embodiment will be described with reference to the drawings. The information processing system of the present example embodiment measures the length of the limb (upper limb/lower limb) of the user using the sensor data measured by the sensor when the user performs a specific motion (also referred to as a measurement motion) with the sensor attached to a predetermined attachment site. In the present example embodiment, the predetermined attachment site is a position of a wrist or an ankle corresponding to a position of a small joint (wrist joint/ankle joint).

(Configuration)

FIG. 1 is a block diagram illustrating an example of a configuration of a measurement system 10 of the present example embodiment. The measurement system 10 includes a data acquisition device 11 and a measurement device 15.

The data acquisition device 11 and the measurement device 15 may be connected by wire or wirelessly. The data acquisition device 11 and the measurement device 15 may be configured by a single device. The measurement system 10 may be configured only by the measurement device 15 by excluding the data acquisition device 11 from the configuration of the measurement system 10.

The data acquisition device 11 is attached to a predetermined attachment site (wrist or ankle) of a person such as a user or a subject. In the present example embodiment, a portion of the wrist or the ankle is referred to as a first attachment site. That is, the data acquisition device 11 is attached to the first attachment site. For example, the data acquisition device 11 is attached to the first attachment site by a wristband, a supporter, taping, a bandage, or the like. The data acquisition device 11 may be built in a device such as a wristwatch or an activity meter. The data acquisition device 11 may be built in an accessory such as a bracelet or an anklet. For example, the data acquisition device 11 may be installed on a glove or a shoe. The data acquisition device 11 may be directly attached to the wrist or the ankle, or may be embedded inside the skin of the wrist or the ankle. For example, the data acquisition device 11 is incorporated in a motion sensor. For example, the data acquisition device 11 is incorporated in an external motion sensor. For example, the data acquisition device 11 is incorporated into a suit type motion sensor integrated with a suit. For example, the data acquisition device 11 may be mounted on a device used near a hand or a foot. The form of the data acquisition device 11 is not particularly limited.

The data acquisition device 11 includes a sensor that measures an acceleration and an angular velocity. The data acquisition device 11 measures accelerations in the three axial directions (also referred to as a spatial acceleration) and angular velocities around the three axes (also referred to as a spatial angular velocity) as physical quantities related to movement of the limb (upper limb/lower limb) of a person. The physical quantity related to the movement of the limb (upper limb/lower limb) measured by the data acquisition device 11 also includes a speed and an angle calculated by integrating the acceleration and the angular velocity. The physical quantity related to the movement of the limb (upper limb/lower limb) measured by the data acquisition device 11 also includes a position (trajectory) calculated by second-order integration of the acceleration. The data acquisition device 11 converts the measured physical quantity into digital data (also referred to as sensor data). The data acquisition device 11 transmits the converted sensor data to the measurement device 15.

The data acquisition device 11 is achieved by, for example, an inertial measurement device including an acceleration sensor and an angular velocity sensor. An example of the inertial measurement device is an inertial measurement unit (IMU). The IMU includes a three-axis acceleration sensor and a three-axis angular velocity sensor. The data acquisition device 11 may include a sensor other than the acceleration sensor and the angular velocity sensor. For example, as another example of the inertial measurement device, there are a vertical gyro (VG) or an attitude heading (AHRS). For example, the global positioning system/inertial navigation system (GPS/INS) is another example of the inertial measurement device.

Figure 2A:
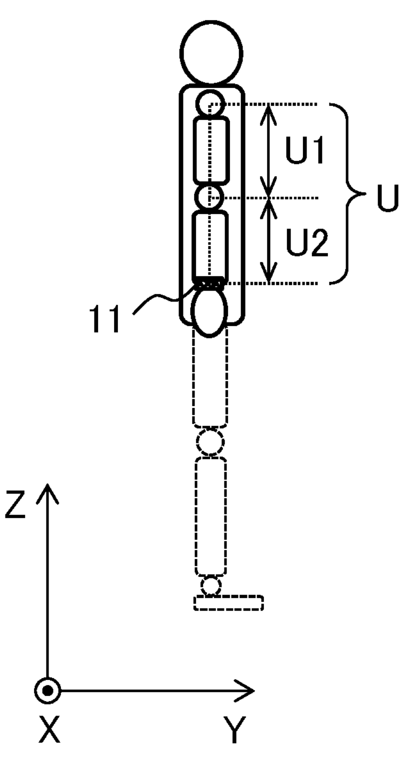
FIG. 2A is a conceptual diagram for describing an attachment example of a data acquisition device of the measurement system according to the first example embodiment.
Figure 2B:
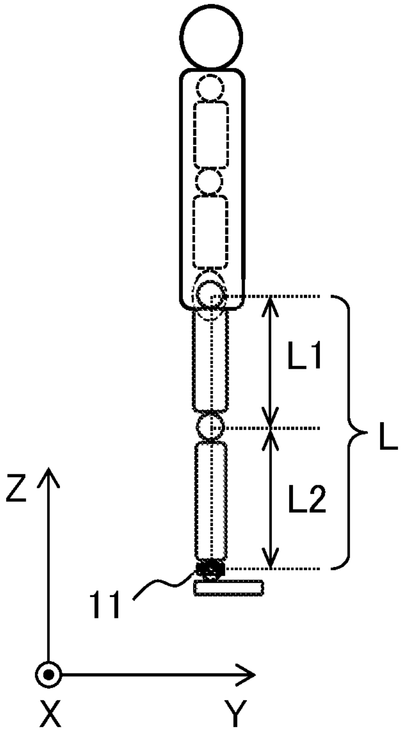
FIG. 2B is a conceptual diagram for describing another attachment example of the data acquisition device of the measurement system according to the first example embodiment.

FIGS. 2A and 2B are conceptual diagrams illustrating an attachment example of the data acquisition device 11. FIG. 2A is a conceptual diagram illustrating an example in which the data acquisition device 11 is attached to the wrist. FIG. 2B is a conceptual diagram illustrating an example in which the data acquisition device 11 is attached to the ankle. FIG. 2 illustrates an example of coordinate axes of a world coordinate system (X axis, Y axis, Z axis) set with respect to the ground. In the present example embodiment, for a user who stands upright and stands still, a left-right direction is defined as an X direction (left is positive), a front-rear direction is defined as a Y direction (front is positive), and a vertical direction is defined as a Z direction (upper is positive).

In the example of FIG. 2A, the data acquisition device 11 is attached to the wrist of the upper limb to be measured. FIG. 2A illustrates an example in which the data acquisition device 11 is attached to the wrist of the right hand. The data acquisition device 11 may be attached to the wrist of the left hand. The data acquisition device 11 may be attached to the wrists of both hands. When the data acquisition device 11 is attached to the wrists of both hands, sensor data regarding the movements of both the right and left upper limbs can be simultaneously acquired. The data acquisition device 11 may be attached to a position other than the wrist. For example, the data acquisition device 11 may be attached at a position of a hand. In this case, the length of the upper limb measured based on the sensor data may be corrected according to the positional relationship between the data acquisition device 11 and the wrist (wrist joint).

In the present example embodiment, the length between the shoulder joint and the wrist joint is defined as a length U of the upper limb. The length between the shoulder joint and the elbow joint is defined as a length U1 of the upper arm. The length between the elbow joint and the wrist joint is defined as a length U2 of the forearm. The sum of the length U1 of the upper arm and the length U2 of the forearm corresponds to the length U of the upper limb. In practice, the distance between the rotation center of the shoulder joint and the attachment site of the data acquisition device 11 is measured as the length U of the upper limb. Therefore, the length U of the upper limb can vary depending on the attachment site of the data acquisition device 11.

In the example of FIG. 2B, the data acquisition device 11 is attached to the ankle of the lower limb to be measured. FIG. 2B illustrates an example in which the data acquisition device 11 is attached to the ankle of the right foot. The data acquisition device 11 may be attached to the ankle of the left foot. The data acquisition devices 11 may be attached to both ankles. When the data acquisition device 11 is attached to the wrists of the feet of both feet, sensor data regarding the movements of both the right and left lower limbs can be simultaneously acquired. The data acquisition device 11 may be attached to a position other than the ankle. For example, the data acquisition device 11 may be attached to a position on the foot or a position on the back of the foot. In this case, the length of the lower limb measured based on the sensor data may be corrected according to the positional relationship between the data acquisition device 11 and the ankle (ankle joint).

In the present example embodiment, the length between the hip joint and the ankle joint is defined as a length L of the lower limb. The length between the hip joint and the knee joint is defined as a length L1 of the thigh. The length between the knee joint and the ankle joint is defined as a length L2 of the lower leg. The sum of the length L1 of the thigh and the length L2 of the lower leg corresponds to the length L of the lower limb. In practice, the distance between the rotation center of the hip joint and the attachment site of the data acquisition device 11 is measured as the length L of the lower limb. Therefore, the length L of the lower limb can vary depending on the attachment site of the data acquisition device 11.

In the present example embodiment, the motion related to the limb (upper limb/lower limb) includes a measurement motion (also referred to as a first measurement motion) around the large joint (shoulder joint/hip joint) and a measurement motion (second measurement motion) around the middle joint (elbow joint/knee joint). That is, the first measurement motion is a rotation motion around a large joint (shoulder joint/hip joint), and the second measurement motion is a rotation motion around a middle joint (elbow joint/knee joint). For example, the sensor data acquired by the data acquisition device 11 according to the movement of the limb (upper limb/lower limb) includes a code (also referred to as an identification code) that can identify the attachment site (wrist/ankle) of the data acquisition device 11 and the type of the measurement motion (first measurement motion/second measurement motion). For example, the sensor data may include an identification code indicating that the data was acquired by the data acquisition device 11 attached to which attachment site (wrist/ankle) in left or right. The format of the sensor data including the identification code is not particularly limited.

Figure 3:
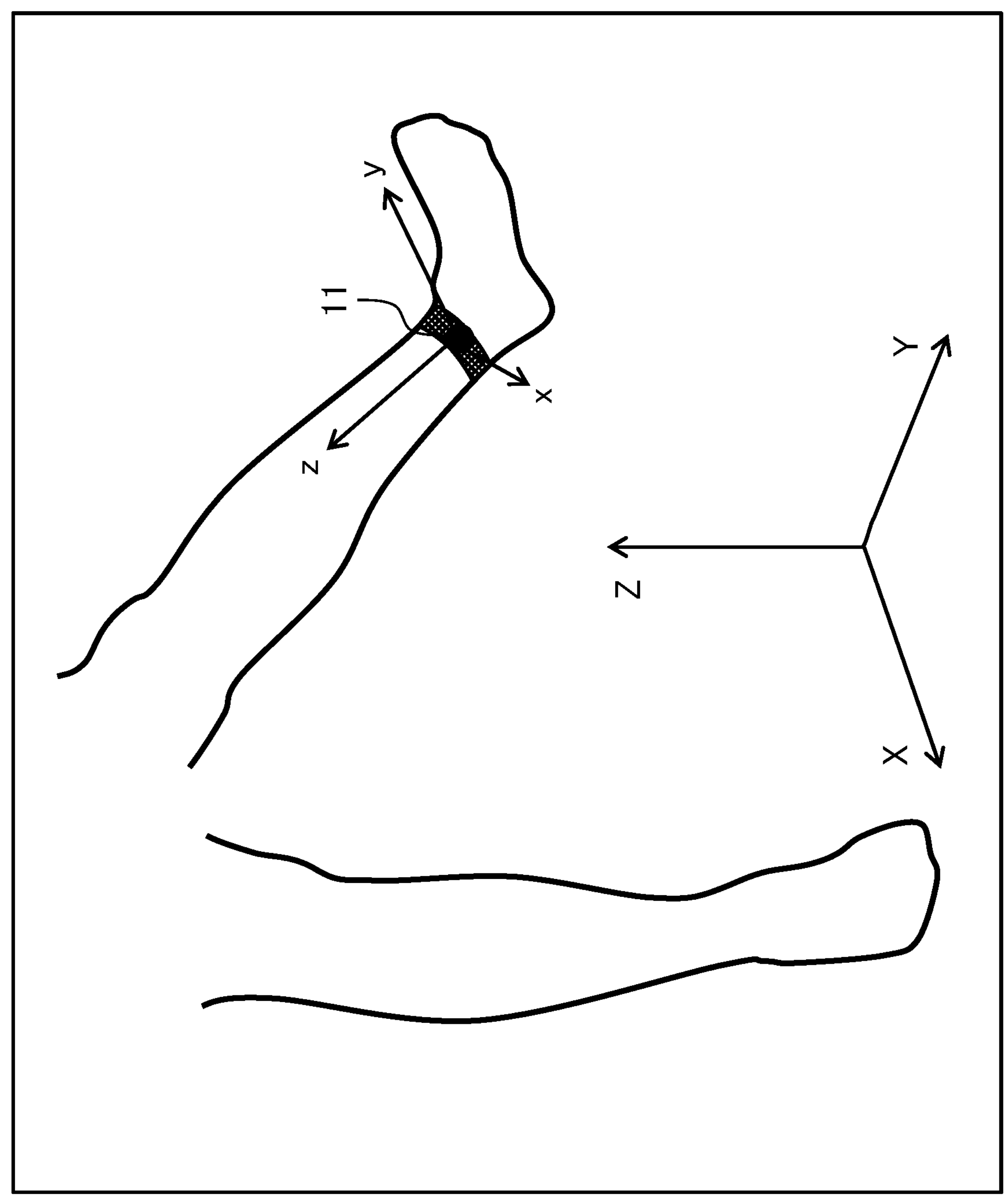
FIG. 3 is a conceptual diagram for describing a coordinate system set in the data acquisition device of the measurement system according to the first example embodiment.

FIG. 3 is a conceptual diagram for describing a local coordinate system (x axis, y axis, z axis) set with respect to the data acquisition device 11 and a world coordinate system (X axis, Y axis, Z axis) set with respect to the ground. In the world coordinate system (X axis, Y axis, Z axis), in a state where the user stands upright and stands still, the lateral direction of the user is set to the X axis direction (the rightward direction is positive), the front direction of the user (the traveling direction) is set to the Y axis direction (the forward direction is positive), and the gravity direction is set to the Z axis direction (the vertically upward direction is positive). The local coordinate system sets a coordinate system including an x direction, a y direction, and a z direction based on the data acquisition device 11. For example, the local coordinate system is set to match the world coordinate system in a state where the user stands upright and stands still. The local coordinate system can be set in any manner as long as the trajectory can be calculated according to the movement of the limb (upper limb/lower limb).

The measurement device 15 acquires sensor data from the data acquisition device 11. The measurement device 15 measures the length of the limb (upper limb/lower limb) using the acquired sensor data. The measurement device 15 estimates the length of the limb (upper limb/lower limb) using sensor data measured according to a measurement motion related to the limb (upper limb/lower limb). For example, the measurement device 15 performs second-order integration on the spatial acceleration included in the sensor data measured according to the measurement motion to calculate the spatial position (trajectory). For example, the measurement device 15 calculates the spatial angle by integrating the spatial angle included in the sensor data measured according to the measurement motion. The measurement device 15 calculates the radius of rotation of the data acquisition device 11 in the period of the measurement motion based on the calculated spatial position (trajectory) and spatial angle. The radius of rotation of the data acquisition device 11 in the period of the measurement motion corresponds to the length related to the limb (upper limb/lower limb). A method of calculating the radius of rotation by the data acquisition device 11 will be described later.

The measurement device 15 calculates the length of the limb (upper limb/lower limb) using the sensor data measured according to the first measurement motion with the large joint (shoulder joint/hip joint) as the rotation center. The measurement device 15 calculates the length of the lower part (forearm/lower leg) of the limb using the sensor data measured according to the second measurement motion with the middle joint (elbow joint/knee joint) as the rotation center. The measurement device 15 calculates the length of the upper part (upper arm/thigh) of the limb by subtracting the length of the lower part (forearm/lower leg) of the limb from the length of the limb (upper limb/lower limb).

The measurement device 15 outputs the calculated the measurement value regarding the limb (upper limb/lower limb). For example, the measurement device 15 outputs a measurement value regarding the limb (upper limb/lower limb) to a display device (not illustrated). For example, the measurement value regarding the limb (upper limb/lower limb) output to the display device is displayed on the screen of the display device. For example, the measurement device 15 outputs a measurement value regarding the limb (upper limb/lower limb) to an external system. For example, the measurement value regarding the limb (upper limb/lower limb) output to the external system is used for any application.

[Data Acquisition Device]

Figure 4:
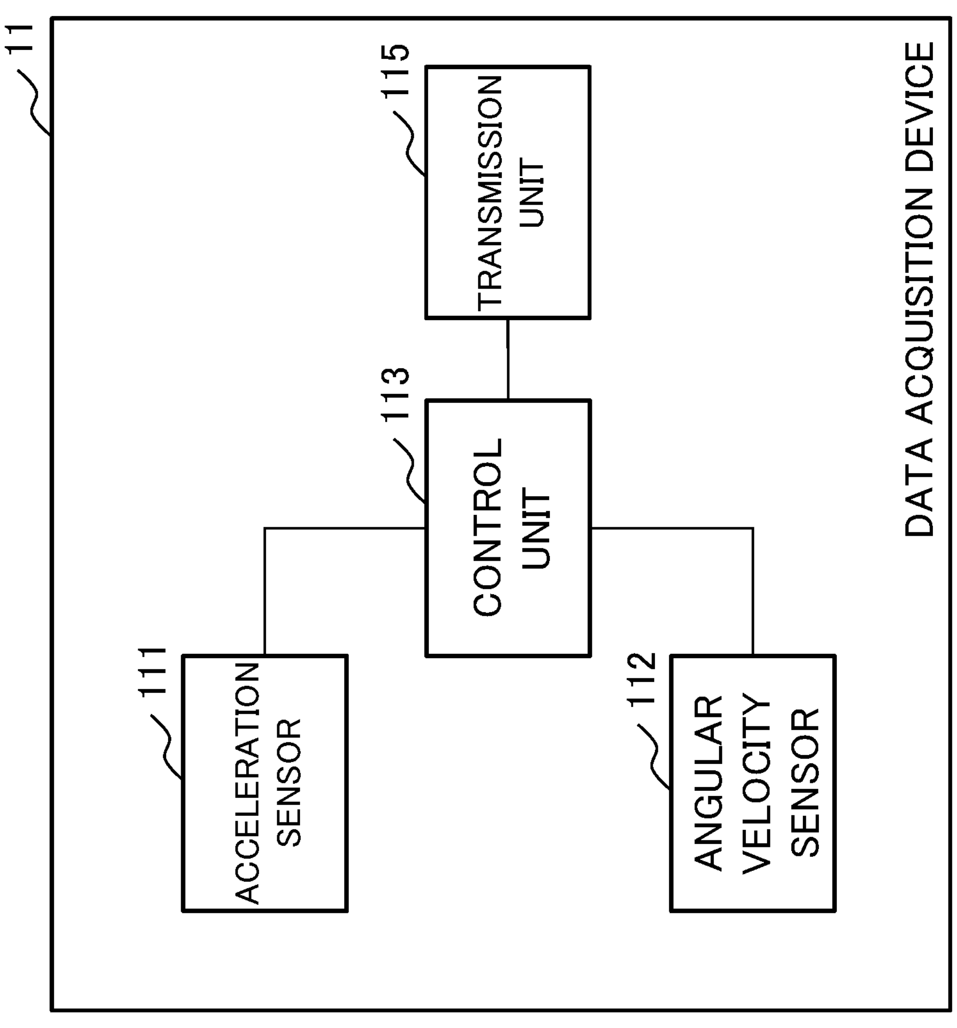
FIG. 4 is a block diagram illustrating an example of a configuration of the data acquisition device of the measurement system according to the first example embodiment.

Next, details of the data acquisition device 11 will be described with reference to the drawings. FIG. 4 is a block diagram illustrating an example of a detailed configuration of the data acquisition device 11. The data acquisition device 11 includes an acceleration sensor 111, an angular velocity sensor 112, a control unit 113, and a transmission unit 115. The data acquisition device 11 includes a power supply (not illustrated). The data acquisition device 11 is attached to a predetermined attachment site (wrist/ankle) of the user to be measured of the limb (upper limb/lower limb).

The acceleration sensor 111 is a sensor that measures acceleration (also referred to as spatial acceleration) in the three axial directions. The acceleration sensor 111 outputs the measured acceleration to the control unit 113. For example, a sensor of a piezoelectric type, a piezoresistive type, a capacitance type, or the like can be used as the acceleration sensor 111. As long as the sensor used for the acceleration sensor 111 can measure an acceleration, the measurement method is not limited.

The angular velocity sensor 112 is a sensor that measures angular velocities around the three axes (also referred to as spatial angular velocities). Angular velocity sensor 112 outputs the measured angular velocity to control unit 113. For example, a sensor of a vibration type, a capacitance type, or the like can be used as the angular velocity sensor 112. As long as the sensor used for the angular velocity sensor 112 can measure an angular velocity, the measurement method is not limited.

The control unit 113 acquires accelerations in the three axial directions from the acceleration sensor 111. The control unit 113 acquires angular velocities around the three axes from the angular velocity sensor 112. The control unit 113 converts the acquired acceleration and angular velocity into digital data. The control unit 113 outputs the converted digital data (also referred to as sensor data) to the transmission unit 115. The sensor data includes at least acceleration data and angular velocity data converted from analog data to digital data. The acceleration data converted into the digital data includes acceleration vectors in the three axial directions. The angular velocity data converted into the digital data includes angular velocity vectors in the three axial directions. The acceleration data and the angular velocity data are associated with acquisition time of the data. For example, an identification code capable of identifying an attachment site (wrist/ankle) of the data acquisition device 11 and a type of the measurement motion (first measurement motion/second measurement motion) is assigned to the sensor data. For example, an identification code indicating that the data was acquired by the data acquisition device 11 attached to which attachment site (wrist/ankle) in left or right is assigned to the sensor data. The identification code may be assigned in the data acquisition device 11 or may be assigned in the measurement device 15. The control unit 113 may be configured to output sensor data obtained by adding correction such as a mounting error, temperature correction, and linearity correction to the acquired acceleration data and angular velocity data. The control unit 113 may be configured to generate speed data and position data (trajectory data) in the three axial directions and angle data around the three axes using the acquired acceleration data and angular velocity data.

For example, the control unit 113 is a microcomputer or a microcontroller that performs control and processing of the data acquisition device 11. For example, the control unit 113 includes a central processing unit (CPU), a random access memory (RAM), a read only memory (ROM), a flash memory, and the like. The control unit 113 controls the acceleration sensor 111 and the angular velocity sensor 112 to measure the angular velocity and the acceleration. For example, the control unit 113 performs analog-to-digital conversion (AD conversion) on physical quantities (analog data) such as the measured angular velocity and acceleration, and stores the converted digital data in the flash memory. The physical quantity (analog data) measured by each of the acceleration sensor 111 and the angular velocity sensor 112 may be converted into digital data in each of the acceleration sensor 111 and the angular velocity sensor 112. The digital data stored in the flash memory is output to the transmission unit 115 at a predetermined timing.

The transmission unit 115 acquires sensor data from the control unit 113. The transmission unit 115 transmits the acquired sensor data to the measurement device 15. The transmission unit 115 may transmit the sensor data to the measurement device 15 via a wire such as a cable, or may transmit the sensor data to the measurement device 15 via wireless communication. For example, the transmission unit 115 is configured to transmit sensor data to the measurement device 15 via a wireless communication function (not illustrated) conforming to a standard such as Bluetooth (registered trademark) or WiFi (registered trademark). The communication function of the transmission unit 115 may conform to a standard other than Bluetooth (registered trademark) or WiFi (registered trademark). The sensor data may be accumulated in a database (not illustrated) without directly transmitting the sensor data from the transmission unit 115 to the measurement device 15. In this case, the measurement device 15 performs measurement regarding the limb (upper limb/lower limb) using the sensor data accumulated in the database.

[Measurement Device]

Figure 5:
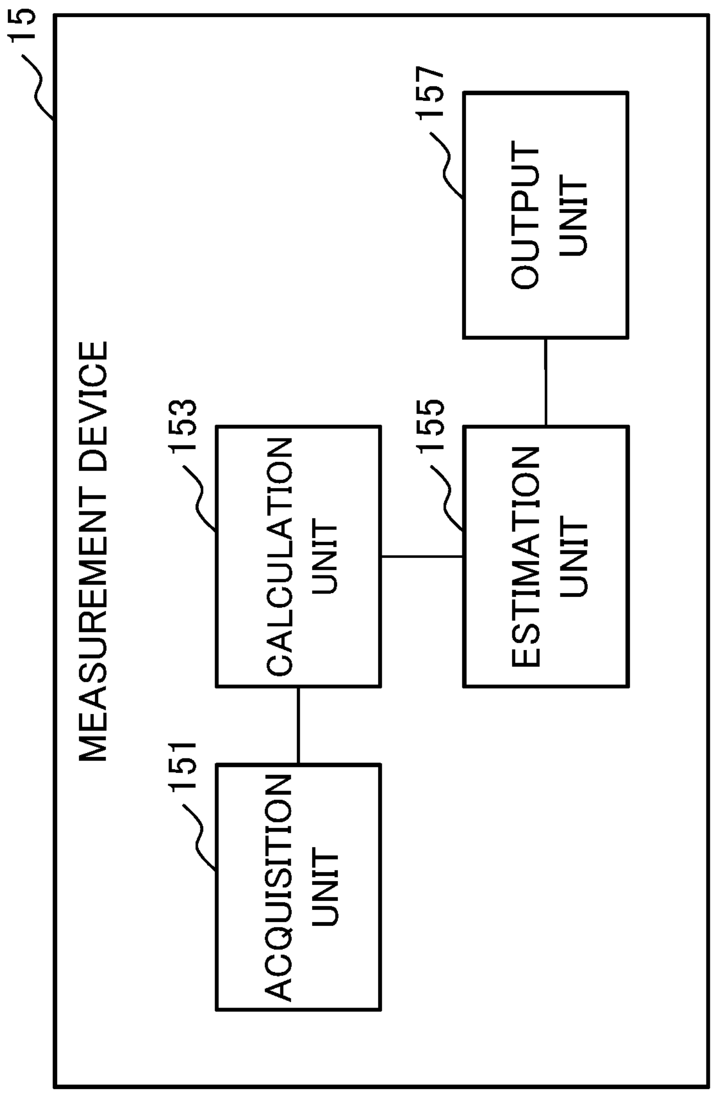
FIG. 5 is a block diagram illustrating an example of a configuration of a measurement device of the measurement system according to the first example embodiment.

Next, details of the measurement device 15 included in the measurement system 10 will be described with reference to the drawings. FIG. 5 is a block diagram illustrating an example of a configuration of the measurement device 15. The measurement device 15 includes an acquisition unit 151, a calculation unit 153, an estimation unit 155, and an output unit 157.

The acquisition unit 151 acquires, from the data acquisition device 11 attached to the first measurement site (wrist/ankle) of the user to be measured of the limb (upper limb/lower limb), sensor data measured according to a measurement motion related to the limb (upper limb/lower limb) of the user. The acquisition unit 151 outputs the acquired sensor data to the calculation unit 153. For example, the acquisition unit 151 receives the sensor data from the data acquisition device 11 via a wire such as a cable. For example, the acquisition unit 151 receives sensor data from the data acquisition device 11 via wireless communication. For example, the acquisition unit 151 receives sensor data from the data acquisition device 11 via a wireless communication function (not illustrated) conforming to a standard such as Bluetooth (registered trademark) or WiFi (registered trademark). The communication function of the acquisition unit 151 may conform to a standard other than Bluetooth (registered trademark) or WiFi (registered trademark). In a case where the sensor data accumulated in the database (not illustrated) is used, the measurement device 15 acquires the sensor data accumulated in the database.

The calculation unit 153 acquires sensor data from the acquisition unit 151. Using the acquired sensor data, the calculation unit 153 calculates the trajectory of the data acquisition device 11 measured according to the measurement motion (first measurement motion/second measurement motion) related to the limb (upper limb/lower limb) of the user. For example, the calculation unit 153 calculates the spatial position (trajectory) by second-order integration of the spatial acceleration measured according to the measurement motion (first measurement motion/second measurement motion) related to the limb (upper limb/lower limb) of the user, the data acquisition device 11 being attached to the first attachment position (wrist/ankle). For example, the calculation unit 153 calculates the spatial angle by integrating the spatial angle included in the sensor data measured according to the measurement motion (first measurement motion/second measurement motion). The calculation unit 153 outputs data (also referred to as trajectory data) regarding the spatial position (trajectory) and the spatial angle to the estimation unit 155.

Figure 6:
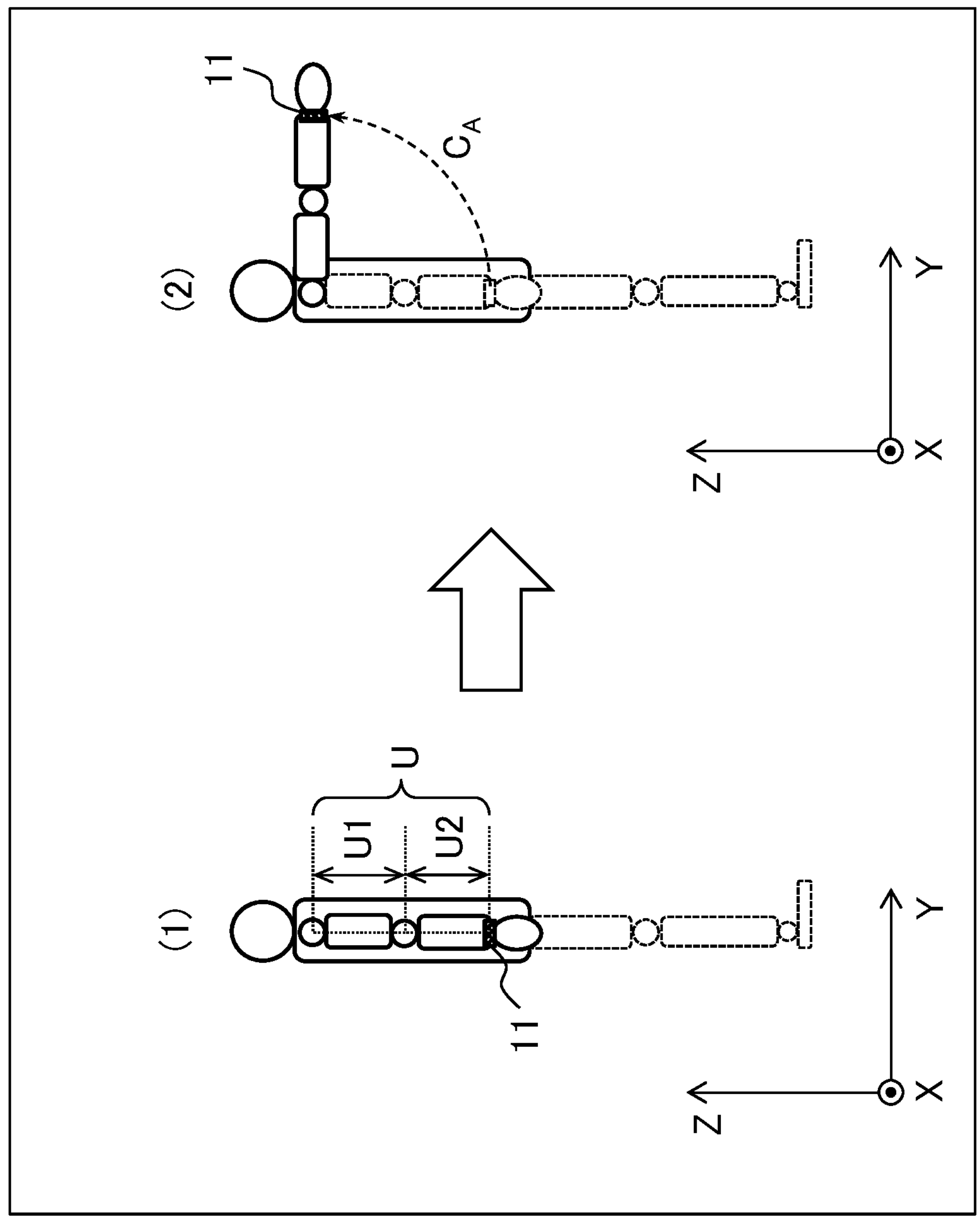
FIG. 6 is a conceptual diagram for describing an example of a first measurement motion of the upper limb according to the first example embodiment.
Figure 7:
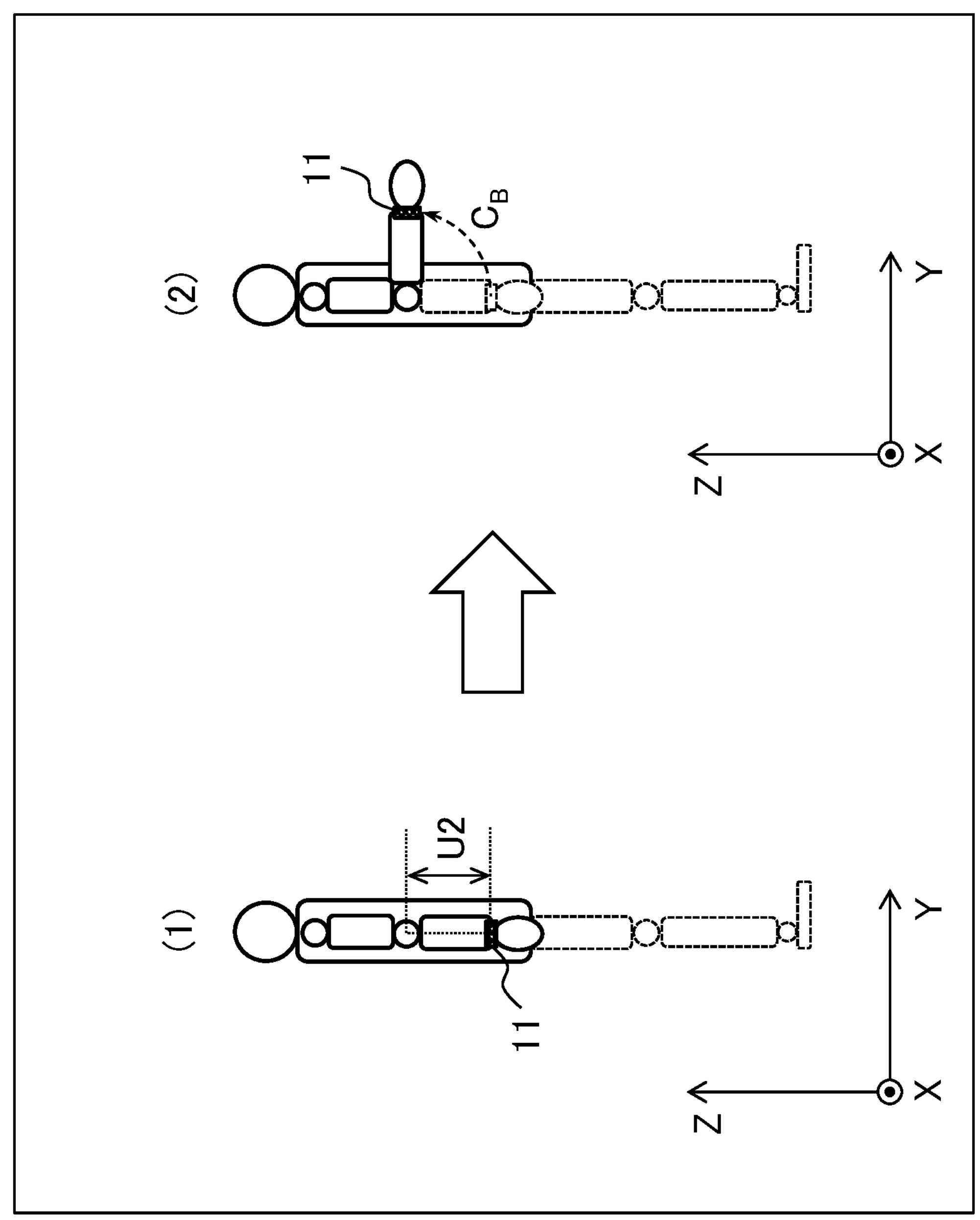
FIG. 7 is a conceptual diagram for describing an example of a second measurement motion of the upper limb according to the first example embodiment.

The measurement motion related to the upper limb will be described with reference to the drawings. FIGS. 6 and 7 are conceptual diagrams for describing a measurement motion related to the upper limb. FIGS. 6 and 7 are views of the user wearing the data acquisition device 11 on the wrist when viewed from the right side. A length from the shoulder joint to the elbow joint (upper arm length) is U1, and a length from the elbow joint to the wrist joint (forearm length) is U2. The length U of the upper limb corresponds to the sum of the length U1 of the upper arm and the length U2 of the forearm.

FIG. 6 is a conceptual diagram for describing the first measurement motion related to the upper limb. FIG. 6(1) illustrates a preparation stage of the first measurement motion. In FIG. 6(1), the user stands upright with the hand facing downward (−Z direction) with the upper limb straightly extended. FIG. 6(2) illustrates a state in which the user performs the first measurement motion. The first measurement motion related to the upper limb is a motion of rotating the upper limb around the shoulder joint in a state where the elbow joint is straight. In the example of FIG. 6, the user rotates the upper limb on the YZ plane (sagittal plane). The calculation unit 153 calculates a trajectory of the data acquisition device 11 at the time of transition from the state of FIG. 6(1) to the state of FIG. 6(2). In the present example embodiment, the first measurement motion regarding the upper limb is regarded as a circular motion drawing an arc $C_A$ (also referred to as a first arc) around the shoulder joint. The first measurement motion related to the upper limb is not limited to be performed on the YZ plane (sagittal plane), but may be performed on the XY plane (horizontal plane) or the ZX plane (coronal plane). The first measurement motion regarding the upper limb may include a mixture of motions on the YZ plane (sagittal plane), the XY plane (horizontal plane), and the ZX plane (coronal plane). When the first measurement motion related to the upper limb is not limited to be performed on be performed on the single plane, the trajectory of the three-dimensional data acquisition device 11 may be calculated. FIG. 6 illustrates an example of transition from the state of FIG. 6(1) to the state of FIG. 6(2). When the rotation motion around the shoulder joint is performed with the upper limb straightly extended, the positions of the start point and the end point of the first measurement motion related to the upper limb are not particularly limited. For example, the upper limb may be reciprocated several times along a similar track. When the upper limb is reciprocated several times, the measurement accuracy regarding the length of the upper limb is improved by averaging the trajectories of the data acquisition device 11. The upper limb may be three-dimensionally rotated in different planes. When the upper limb is three-dimensionally rotated, the trajectory of the data acquisition device 11 may be regarded as a spherical surface.

FIG. 7 is a conceptual diagram for describing a second measurement motion related to the upper limb. FIG. 7(1) illustrates a preparation stage of the second measurement motion. In FIG. 7(1), the user stands upright with the hand facing downward (−Z direction) with the upper limb straightly extended. FIG. 7(2) illustrates a state in which the user performs the second measurement motion. The second measurement motion related to the upper limb is a motion of rotating the forearm around the elbow joint with the upper arm on the body side. In the example of FIG. 7, the user rotates the forearm on the YZ plane (sagittal plane). The calculation unit 153 calculates the trajectory of the data acquisition device 11 at the time of transition from the state of FIG. 7(1) to the state of FIG. 7(2). In the present example embodiment, the second measurement motion related to the upper limb is regarded as a circular motion drawing an arc $C_B$ (also referred to as a second arc) around the elbow joint. The second measurement motion related to the upper limb is not limited to be performed on the YZ plane (sagittal plane), but may be performed on the XY plane (horizontal plane) or the ZX plane (coronal plane). The second measurement motion regarding the upper limb may include a mixture of motions on the YZ plane (sagittal plane), the XY plane (horizontal plane), and the ZX plane (coronal plane). When the second measurement motion related to the upper limb is not limited to be performed on the single plane, the trajectory of the three-dimensional data acquisition device 11 may be calculated. FIG. 7 illustrates an example of transition from the state of FIG. 7(1) to the state of FIG. 7(2). The positions of the start point and the end point of the second measurement motion related to the upper limb are not particularly limited as long as the rotation motion around the elbow joint is performed with the upper arm on the body side. For example, the forearm may be reciprocated several times along a similar trajectory. When the forearm is reciprocated several times, the measurement accuracy regarding the length of the forearm is improved by averaging the trajectories of the data acquisition device 11.

Figure 8:
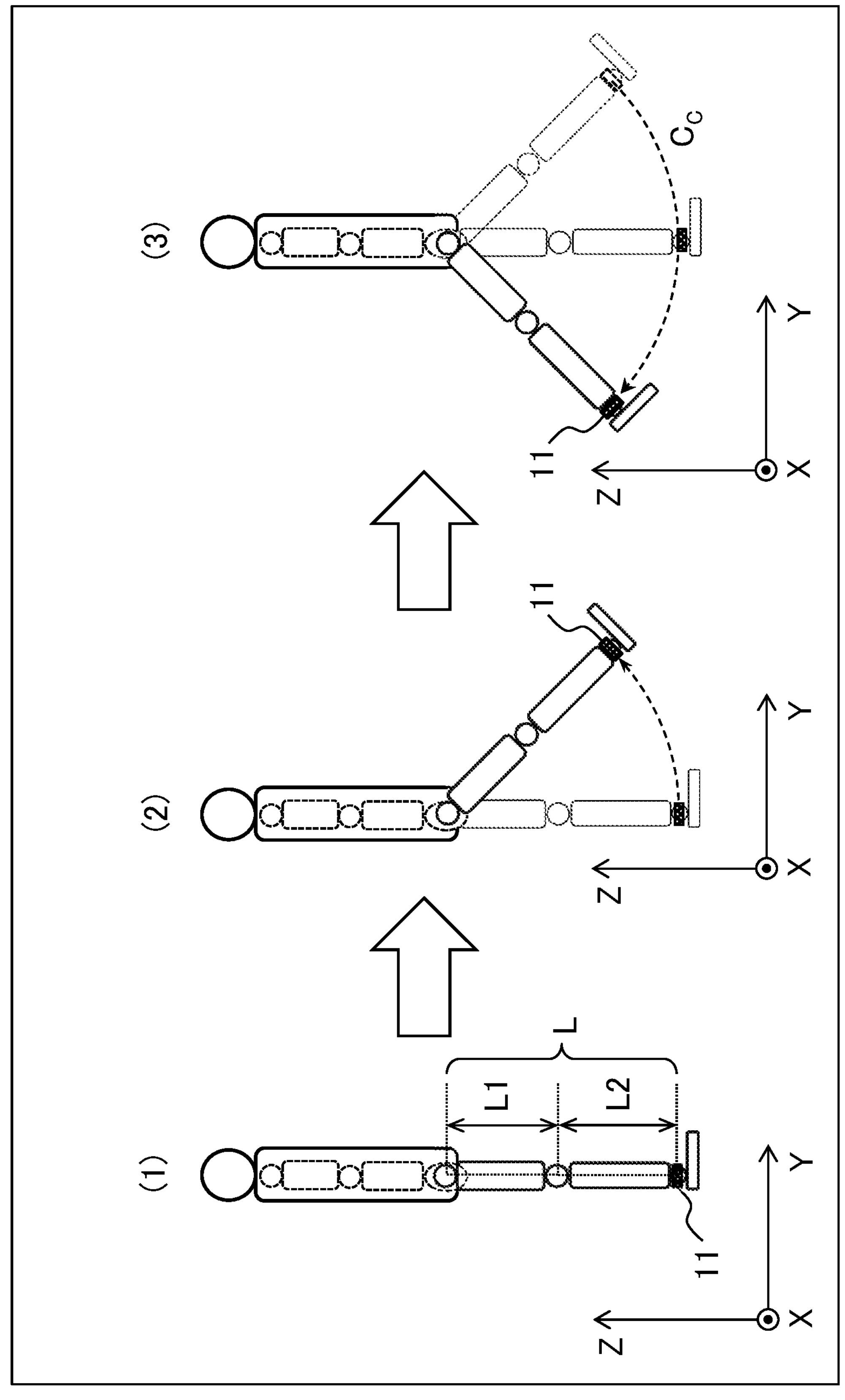
FIG. 8 is a conceptual diagram for describing an example of a first measurement motion of the lower limb according to the first example embodiment.
Figure 9:
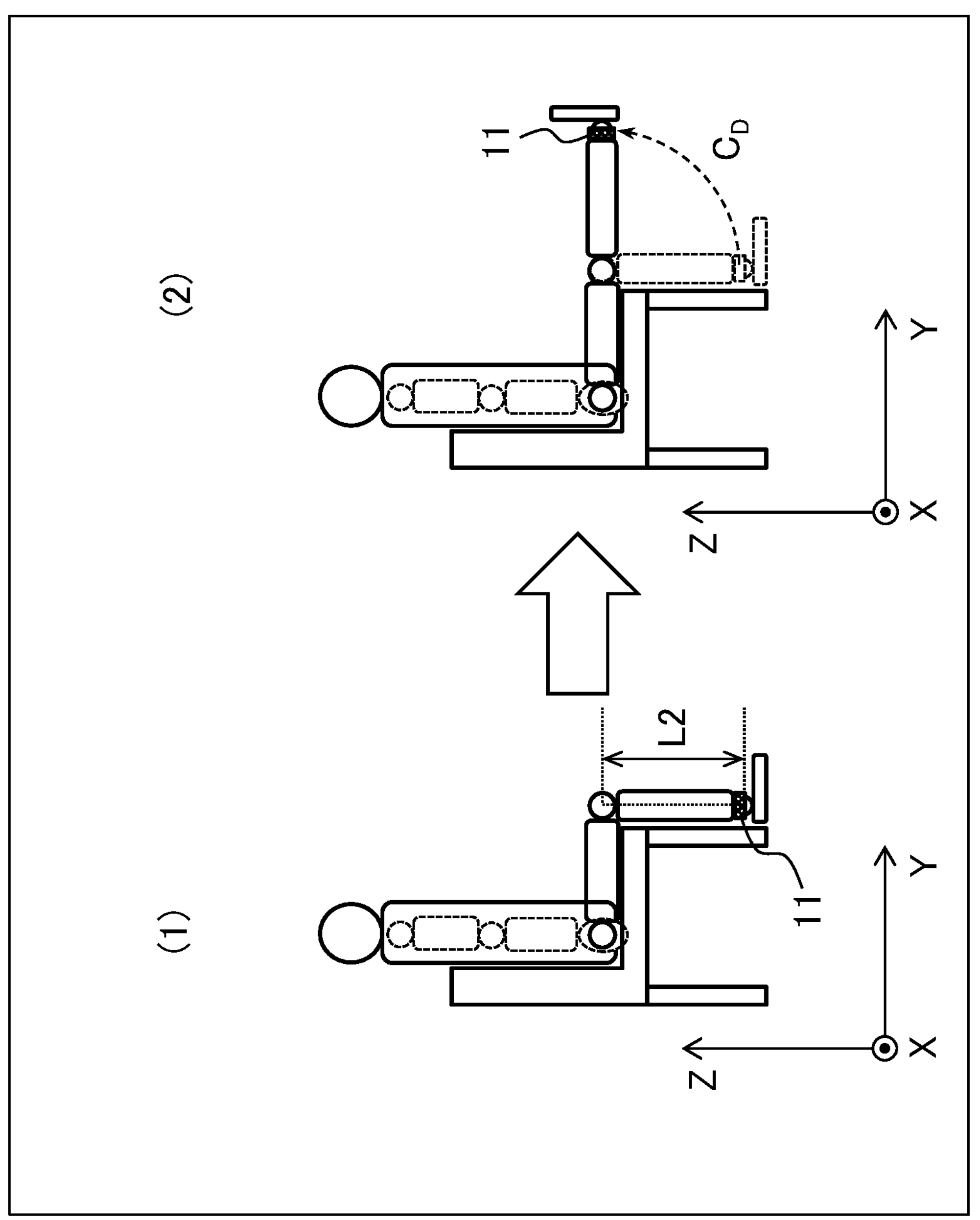
FIG. 9 is a conceptual diagram for describing an example of a second measurement motion of the lower limb according to the first example embodiment.

Next, a measurement motion related to the lower limb will be described with reference to the drawings. FIGS. 8 and 9 are conceptual diagrams for describing a measurement motion related to a lower limb. FIGS. 8 and 9 are views of the user wearing the data acquisition device 11 on the ankle when viewed from the right side. Hereinafter, a length from the hip joint to the knee joint (thigh length) is L1, and a length from the knee joint to the ankle joint (lower leg length) is L2. The length L of the lower limb corresponds to the sum of the length L1 of the thigh and the length L2 of the lower leg.

FIG. 8 is a conceptual diagram for describing a first measurement motion related to the lower limb. FIG. 8(1) illustrates a preparation stage of the first measurement motion. In FIG. 8(1), the user stands upright with the lower limb straightly extended. FIGS. 8(2) and 8(3) illustrate a state in which the user performs the first measurement motion. FIG. 8(2) illustrates a state in which the right foot kicks forward (+Y direction). FIG. 8(3) illustrates a state in which the right foot kicking forward (+Y direction) is pulled backward (−Y direction). The first measurement motion related to the lower limb is a motion of rotating the lower limb around the hip joint in a state where the knee joint is straight. In the example of FIG. 8, the user rotates the lower limb on the YZ plane (sagittal plane). The calculation unit 153 calculates the trajectory of the data acquisition device 11 at the time of transition from the state of FIG. 8(1) to the state of FIG. 8(2) and then to the state of FIG. 8(3). In the present example embodiment, the first measurement motion related to the lower limb is regarded as a circular motion drawing an arc Cc (also referred to as a first arc) around the hip joint. The first measurement motion related to the lower limb is not limited to be performed on the YZ plane (sagittal plane), but may be performed on the XY plane (horizontal plane) or the ZX plane (coronal plane). The first measurement motion related to the lower limb may include a mixture of motions on the YZ plane (sagittal plane), the XY plane (horizontal plane), and the ZX plane (coronal plane). When the first measurement motion related to the lower limb is not limited to be performed on a single plane, the trajectory of the three-dimensional data acquisition device 11 may be calculated. FIG. 8 illustrates an example of transition from the state of FIG. 8(1) to the state of FIG. 8(2) and then to the state of FIG. 8(3). As long as the rotation motion around the hip joint is performed with the lower limb straightly extended, the positions of the start point and the end point of the first measurement motion related to the lower limb are not particularly limited. For example, the lower limb may be reciprocated along a similar track. When the lower limb is reciprocated several times, the measurement accuracy regarding the length of the lower limb is improved by averaging the trajectories of the data acquisition device 11. The lower limb may be three-dimensionally rotated in different planes. When the lower limb is three-dimensionally rotated, the trajectory of the data acquisition device 11 may be regarded as a spherical surface.

FIG. 9 is a conceptual diagram for describing a second measurement motion related to the lower limb. FIG. 9(1) illustrates a preparation stage of the second measurement motion. In FIG. 9(1), the user sits on a chair with the lower leg substantially parallel to the Z direction. FIG. 9(2) illustrates a state in which the user is performing the second measurement motion. The second measurement motion related to the lower limb is a motion of rotating the lower leg around the knee joint while sitting on a chair. In the example of FIG. 9, the user rotates the lower leg on the YZ plane (sagittal plane). The calculation unit 153 calculates the trajectory of the data acquisition device 11 at the time of transition from the state of FIG. 9(C1) to the state of FIG. 9(C2). In the present example embodiment, the second measurement motion related to the lower limb is regarded as a circular motion drawing an arc $C_D$ (also referred to as a second arc) around the knee joint. The second measurement motion related to the lower limb is not limited to be performed on the YZ plane (sagittal plane), but may be performed on the XY plane (horizontal plane) or the ZX plane (coronal plane). The second measurement motion related to the lower limb may include a mixture of motions on the YZ plane (sagittal plane), the XY plane (horizontal plane), and the ZX plane (coronal plane). In a case where the second measurement motion related to the lower limb is not limited to be performed on a single plane, the trajectory of the three-dimensional data acquisition device 11 may be calculated. FIG. 9 illustrates an example of transition from the state of FIG. 9(1) to the state of FIG. 9(2). As long as the rotation motion around the knee joint is performed, the positions of the start point and the end point of the second measurement motion related to the lower limb are not particularly limited. For example, the lower leg may be reciprocated along a similar track. When the lower leg is reciprocated several times, the measurement accuracy regarding the length of the lower leg is improved by averaging the trajectories of the data acquisition device 11. In the case of the rotation motion around the knee joint, the second measurement motion related to the lower limb may be performed not in the state of sitting on a chair but in a one-leg standing posture, a posture leaning against a wall, or a lying posture.

The estimation unit 155 acquires a trajectory (also referred to as trajectory data) regarding the limb (upper limb/lower limb) from the calculation unit 153 based on sensor data measured according to a measurement motion regarding the limb (upper limb/lower limb). The estimation unit 155 estimates the length of the limb (upper limb/lower limb) based on the acquired trajectory regarding the limb (upper limb/lower limb). For example, the estimation unit 155 calculates the radius of rotation of the data acquisition device 11 during the measurement motion based on the calculated spatial position (trajectory) and spatial angle. The radius of rotation of the data acquisition device 11 during the measurement motion corresponds to the length related to the limb (upper limb/lower limb).

The estimation unit 155 calculates the length of the limb (upper limb/lower limb) using sensor data measured according to the first measurement motion with the large joint (shoulder joint/hip joint) as the rotation center. The estimation unit 155 calculates the length of the lower part (forearm/lower leg) of the limb using the sensor data measured according to the second measurement motion with the middle joint (elbow joint/knee joint) as the rotation center. The estimation unit 155 calculates the length of the upper part (upper arm/thigh) of the limb by subtracting the length of the lower part (forearm/lower leg) of the limb from the length of the limb (upper limb/lower limb).

Figure 10:
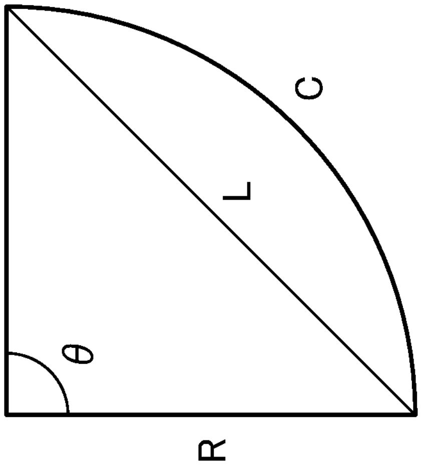
FIG. 10 is a conceptual diagram for describing an example of calculation of the length of the limb by the measurement device of the measurement system according to the first example embodiment.

FIG. 10 is a conceptual diagram for describing an example of calculating the radius of rotation of the data acquisition device 11 during the measurement motion based on the spatial position (trajectory) and the spatial angle. In the measurement motion, a rotation motion around a large joint (shoulder joint/hip joint) and a middle joint (elbow joint/knee joint) is performed.

For example, the estimation unit 155 calculates the length (radius R in FIG. 10) related to the limb (upper limb/lower limb) using the trajectory (arc C in FIG. 10) of the data acquisition device 11 and the distance (chord length L in FIG. 10) between the positions of the data acquisition device 11 at the start point and the end point in the measurement motion. For example, the estimation unit 155 calculates the length (radius R) regarding the limb (upper limb/lower limb) based on the relational expression of Expression 1 below.

$$\frac{L}{2} = R\sin\left(\frac{C}{2R}\right) \tag{1}$$

The estimation unit 155 calculates the radius R as the length related to the limb (upper limb/lower limb) based on Expression 1 above.

For example, the estimation unit 155 calculates the length (radius R in FIG. 10) regarding the limb (upper limb/lower limb) using the trajectory (arc C in FIG. 10) of the data acquisition device 11 and the spatial angle (central angle θ in FIG. 10) in the circular orbit of the data acquisition device 11. For example, the estimation unit 155 calculates the length (radius R) regarding the limb (upper limb/lower limb) using the relational expression of Expression 2 below.

$$R = \frac{180}{\theta} \times \frac{C}{\pi} \tag{2}$$

By using Expression 2 above, the radius R can be calculated as the length related to the limb (upper limb/lower limb).

For example, the estimation unit 155 may divide the trajectory of the data acquisition device 11 according to the measurement motion into a plurality of sections, and obtain the length regarding the limb (upper limb/lower limb) using the radius of curvature calculated for each section.

Figure 11:
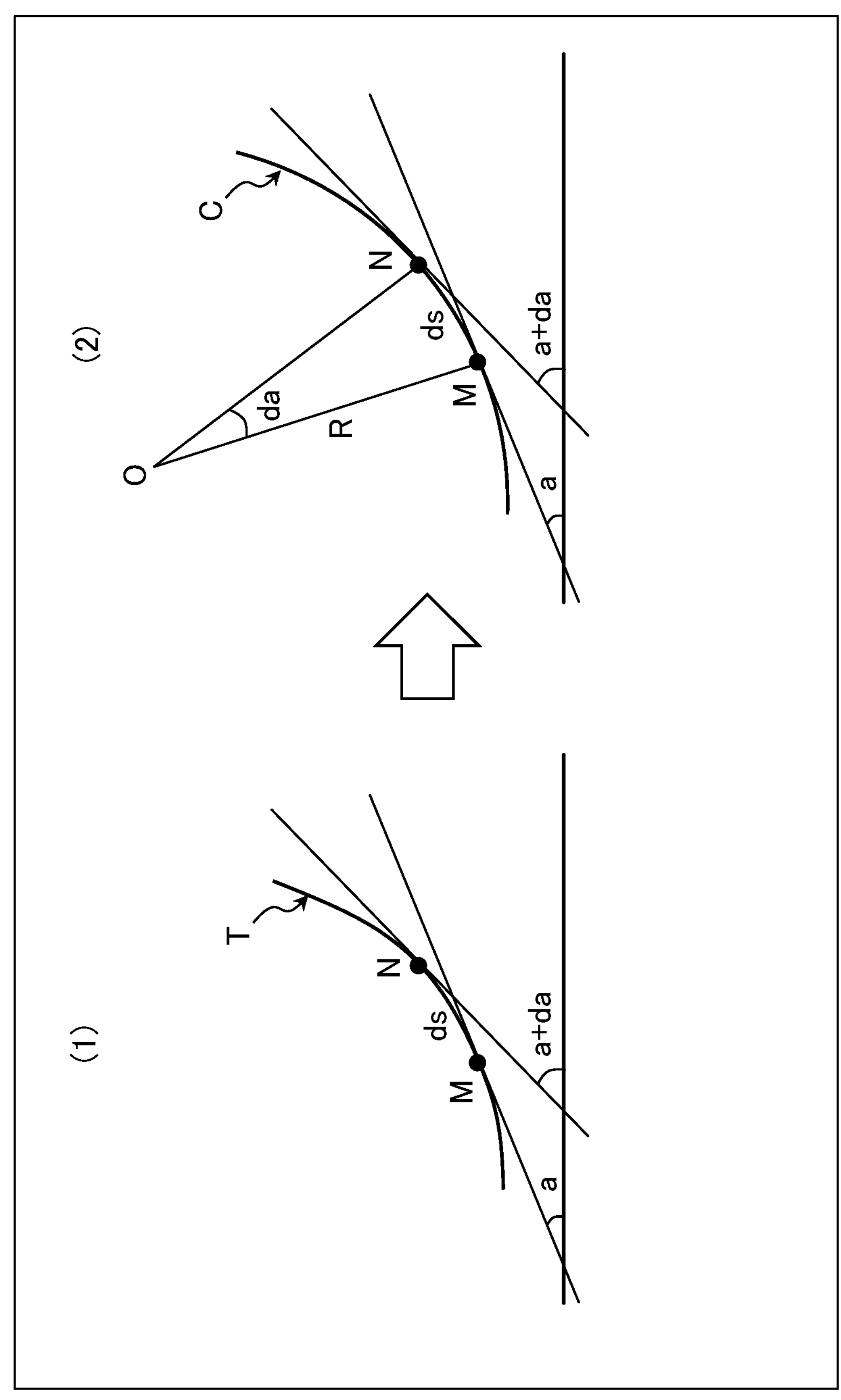
FIG. 11 is a conceptual diagram for describing another example of calculation of the length of the limb by the measurement device of the measurement system according to the first example embodiment.

FIG. 11 is a conceptual diagram for describing an example in which the trajectory T of the data acquisition device 11 is divided into minute steps ds, and the length regarding the limb (upper limb/lower limb) is estimated using the radius of curvature R calculated for each minute step ds. FIG. 11(1) illustrates an example of the minute step ds set on the trajectory T of the data acquisition device 11. It is assumed that the minute step ds in the section between the point M and the point N has a sufficiently minute length, and the trajectory T can be approximated to the arc C in the section of the minute step ds. The inclination of the tangent of the trajectory T at the point M is a, and the inclination of the tangent of the trajectory T at the point N is a+da. That is, the difference between the inclination of the tangent of the trajectory T at the point M and the inclination of the tangent of the trajectory T at the point N is denoted by da. FIG. 11(2) illustrates an example in which an arc C having a central angle da is fitted to a minute step ds in a section between a point M and a point N. The radius of curvature R of the arc C of FIG. 11(2) corresponds to the length related to the limb (upper limb/lower limb).

For example, the estimation unit 155 calculates the radius of curvature R using Expression 3 below.

$$R = \frac{ds}{da} \tag{3}$$

For example, when the radius of curvature R is obtained by converging the minute step ds and the central angle da to 0, the length regarding the limb (upper limb/lower limb) can be calculated with high accuracy.

Figure 12:
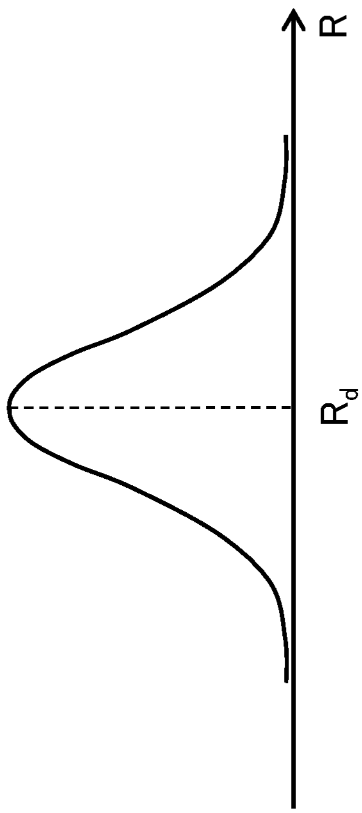
FIG. 12 is a conceptual diagram for describing another example of calculation of the length of the limb by the measurement device of the measurement system according to the first example embodiment.

In the example of FIG. 11, the estimation unit 155 estimates the length regarding the limb (upper limb/lower limb) based on the distribution of the radii of curvature of the plurality of sections. For example, in the frequency distribution in which the radius of curvature is on the horizontal axis and the frequency of the radius of curvature is on the vertical axis, the estimation unit 155 estimates the radius of curvature having the largest frequency as the length regarding the limb (upper limb/lower limb). FIG. 12 is an example of a frequency distribution curve in which the radius of curvature is on the horizontal axis and the frequency of the radius of curvature is on the vertical axis. For example, the estimation unit 155 estimates the arithmetic mean Rd of the curvature radii of the plurality of sections as the length related to the limb (upper limb/lower limb). For example, the estimation unit 155 may estimate the geometric average of the curvature radii of the plurality of sections as the length regarding the limb (upper limb/lower limb). For example, the estimation unit 155 may estimate a representative value such as a median value or a mode of the radii of curvature of the plurality of sections as the length related to the limb (upper limb/lower limb).

The output unit 157 outputs the measurement value regarding the limb (upper limb/lower limb) estimated by the estimation unit 155. For example, the output unit 157 outputs the measurement value related to limb (upper limb/lower limb) to a display device (not illustrated). For example, the measurement value regarding the limb (upper limb/lower limb) output to the display device is displayed on the screen of the display device. For example, the output unit 157 outputs a measurement value related to limb (upper limb/lower limb) to an external system. For example, the measurement value regarding the limb (upper limb/lower limb) output to the external system is used for any application.

(Operation)

Next, an operation of the measurement system 10 of the present example embodiment will be described with reference to the drawings. An example of the operation of the measurement device 15 of the measurement system 10 will be described with reference to a flowchart. The measurement motion regarding the upper limb and the measurement motion regarding the lower limb will be separately described. In the following, an example in which the measurement regarding the upper limb and the measurement regarding the lower limb is separately performed will be described, but the measurement regarding the upper limb and the measurement regarding the lower limb may be performed in the same flow.

[Measurement of Upper Limb]

Figure 13:
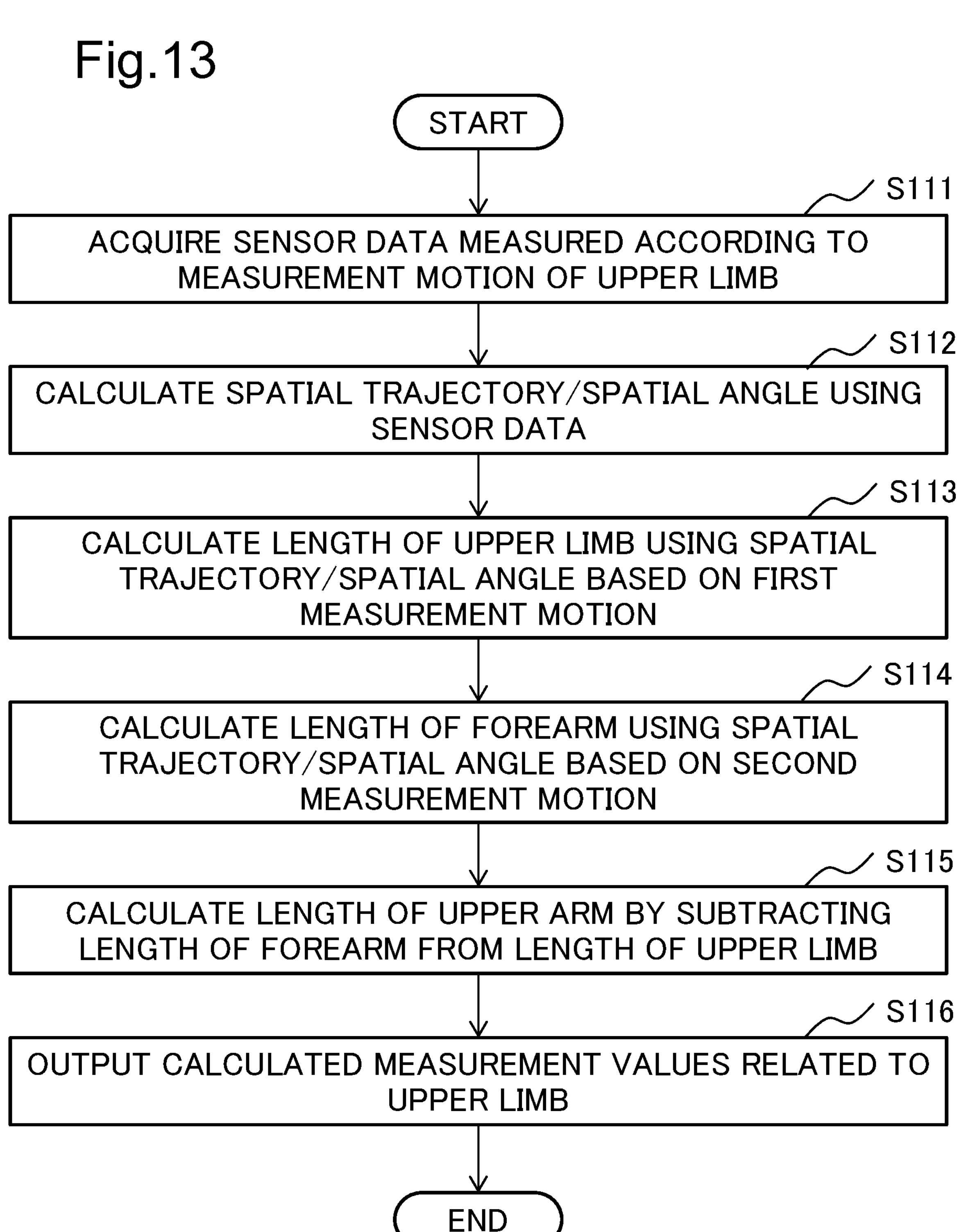
FIG. 13 is a flowchart for describing an example of measurement of the length of the upper limb by the measurement device of the measurement system according to the first example embodiment.

FIG. 13 is a flowchart for describing an example of the operation of the measurement device 15 in the measurement related to the upper limb. In the description along the flowchart of FIG. 13, the measurement device 15 will be described as an operation subject.

In FIG. 13, first, the measurement device 15 acquires sensor data measured according to the measurement motion of the upper limb (first measurement motion/second measurement motion) from the data acquisition device 11 (step S111).

Next, the measurement device 15 calculates the spatial trajectory/spatial angle using the acquired sensor data (step S112).

Next, the measurement device 15 calculates the length of the upper limb using the spatial trajectory/spatial angle based on the first measurement motion (step S113).

Next, the measurement device 15 calculates the length of the forearm using the spatial trajectory/spatial angle based on the second measurement motion (step S114). The order of the processing of step S113 and step S114 may be switched.

Next, the measurement device 15 calculates the length of the upper arm by subtracting the length of the forearm from the length of the upper limb (step S115).

Next, the measurement device 15 outputs the calculated values of the lengths of the upper limbs, the upper arm, and the forearm (also referred to as measurement values regarding the upper limb) (step S116).

The measurement values regarding the upper limb output from the measurement device 15 is used according to the application.

[Measurement of Lower Limb]

FIG. 14 is a flowchart for describing an example of the operation of the measurement device 15 in the measurement regarding the lower limb. In the description along the flowchart of FIG. 14, the measurement device 15 will be described as an operation subject.

In FIG. 14, first, the measurement device 15 acquires sensor data measured according to the measurement motion of the lower limb (first measurement motion/second measurement motion) from the data acquisition device 11 (step S121).

Next, the measurement device 15 calculates the spatial trajectory/spatial angle using the acquired sensor data (step S122).

Next, the measurement device 15 calculates the length of the lower limb using the spatial trajectory/spatial angle based on the first measurement motion (step S123).

Next, the measurement device 15 calculates the length of the lower leg using the spatial trajectory/spatial angle based on the second measurement motion (step S124). The order of the processing of step S123 and step S124 may be switched.

Next, the measurement device 15 calculates the thigh length by subtracting the lower leg length from the lower limb length (step S125).

Next, the measurement device 15 outputs the calculated values of the lengths of the lower limbs, the thigh, and the lower leg (also referred to as measurement values regarding the lower limb) (step S126). The measurement values regarding the lower limb output from the measurement device 15 is used according to the application.

First Application Example

Next, the first application example according to the present example embodiment will be described with reference to the drawings. In the present application example, it is assumed that a user performs a measurement motion according to an instruction displayed on a display unit of a mobile terminal in which an application (also referred to as an "appli") having a function of the measurement device of the present example embodiment is installed. In the present application example, a mobile terminal is used, but any terminal device can be used as long as the screen can be disposed at a position visually recognizable by the user.

Figure 15:
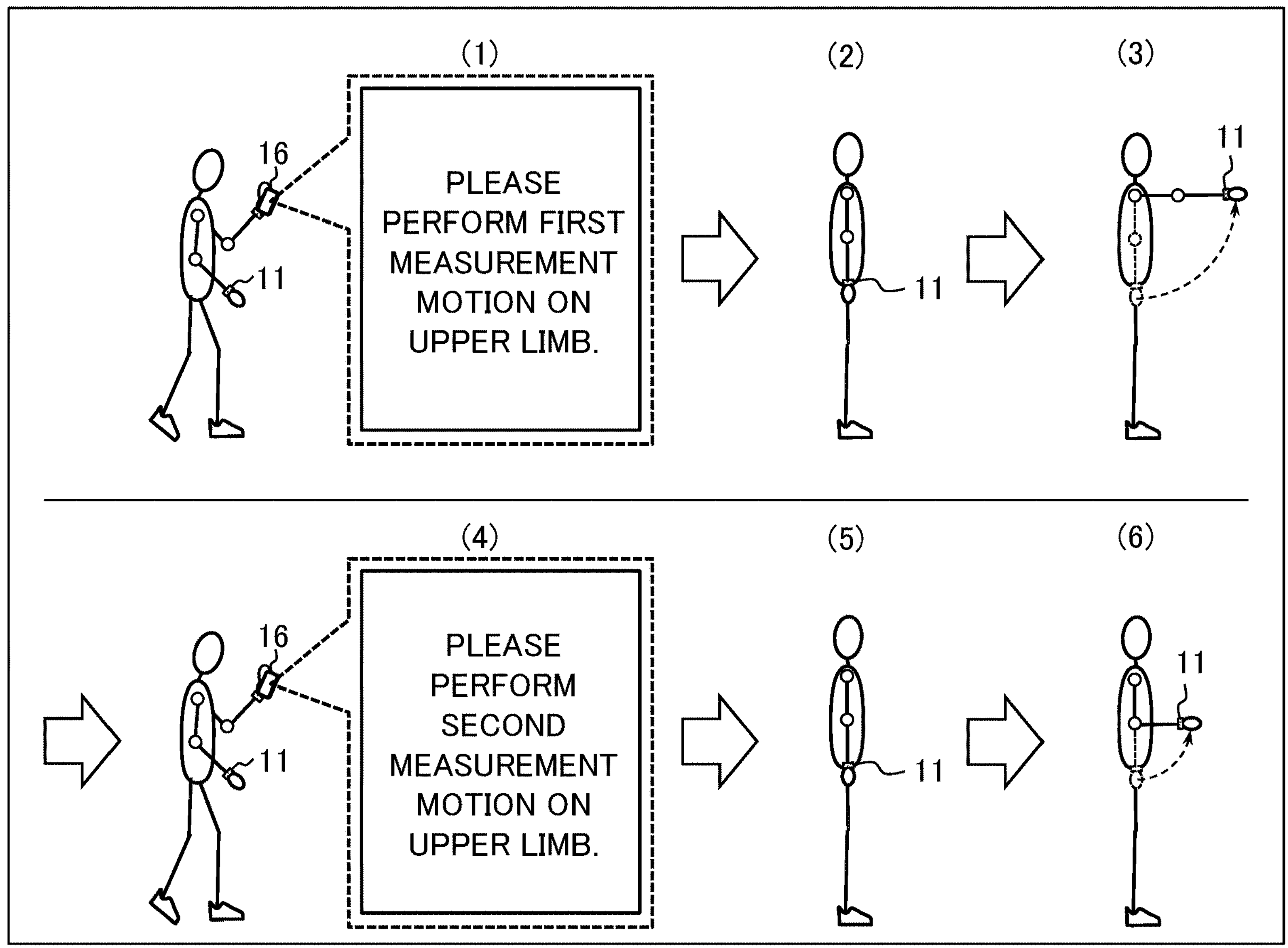
FIG. 15 is a conceptual diagram for describing measurement regarding the upper limb in a first application example according to the first example embodiment.

FIG. 15 is a conceptual diagram for describing measurement related to the upper limb. In the example of FIG. 15, the user wears the data acquisition device 11 on the wrist. For example, an instruction to wear the data acquisition device 11 on the wrist may be displayed on the screen of a mobile terminal 160. The user performs the measurement motion related to the upper limb according to the instruction displayed on the screen of the mobile terminal 160. In the example of FIG. 15, an example of the measurement motion of the right hand is illustrated. The measurement motion of the left hand can also be performed in the same manner as the right hand.

FIG. 15(1) illustrates a situation in which the user to be measured of the limb visually recognizes the instruction that "Please perform the first measurement motion related to the upper limb" displayed on the screen of the mobile terminal 160. FIG. 15(2) illustrates a state in which the user according to the instruction displayed on the screen of the mobile terminal 160 is stationary in preparation for the first measurement motion related to the upper limb. FIG. 15(3) illustrates a state in which the user performs a rotation motion around the shoulder joint as the first measurement motion. FIG. 15(4) illustrates a situation in which the user who has completed the first measurement motion related to the upper limb visually recognizes the instruction that "Please perform the second measurement motion related to the upper limb" displayed on the screen of the mobile terminal 160. FIG. 15(5) illustrates a state in which the user according to the instruction displayed on the screen of the mobile terminal 160 is stationary in preparation for the second measurement motion related to the upper limb. FIG. 15(6) illustrates a state in which the user performs a rotation motion around the elbow joint as the second measurement motion.

Figure 16:
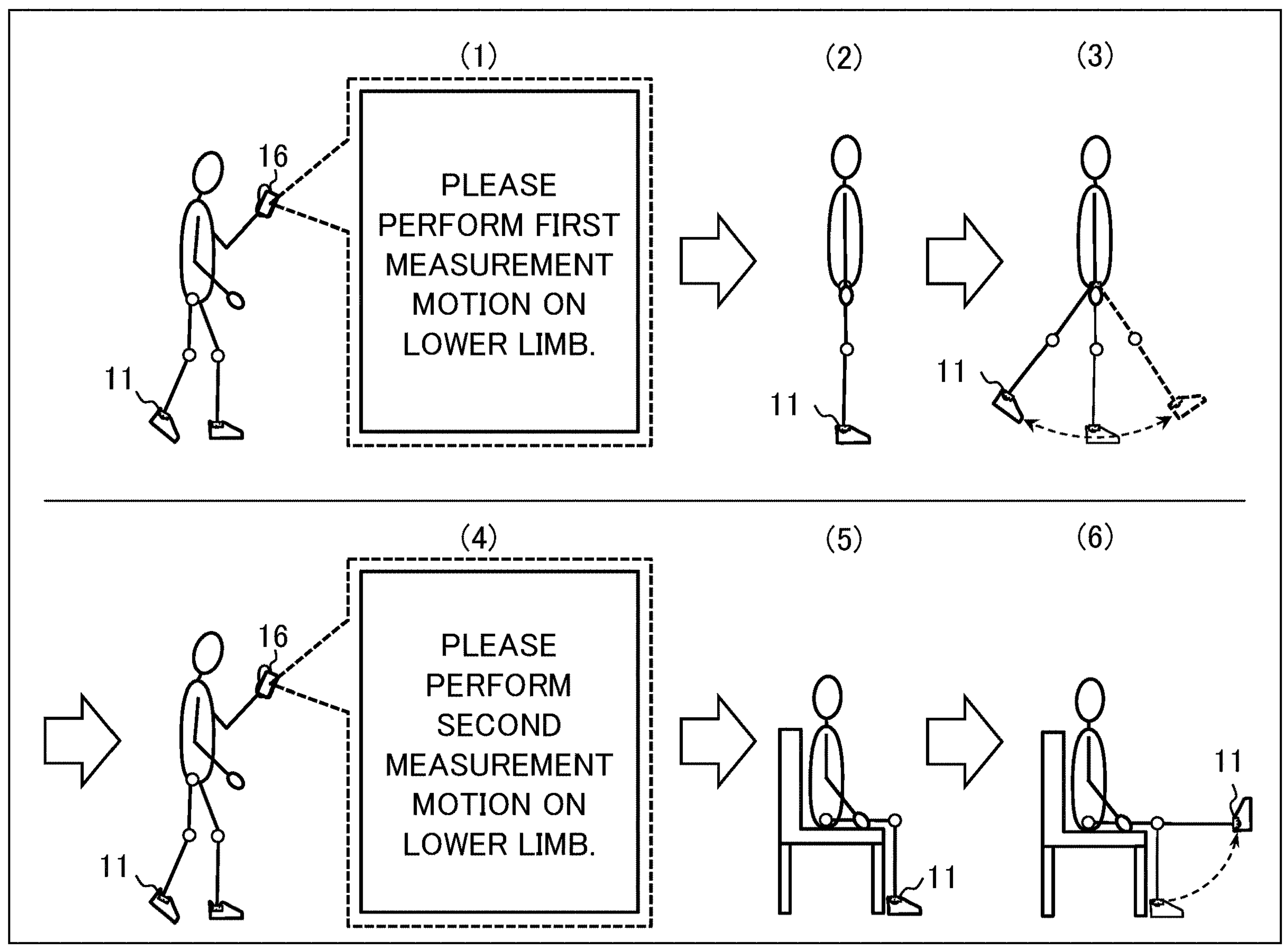
FIG. 16 is a conceptual diagram for describing measurement regarding the lower limb in the first application example according to the first example embodiment.

FIG. 16 is a conceptual diagram for describing measurement related to a lower limb. In the example of FIG. 16, the user wears the data acquisition device 11 on the ankle. For example, an instruction to wear the data acquisition device 11 on the ankle may be displayed on the screen of the mobile terminal 160. The user performs the measurement motion related to the lower limb according to the instruction displayed on the screen of the mobile terminal 160. In the example of FIG. 16, an example of a measurement motion of the right foot is illustrated. The measurement motion of the left foot can also be performed in the same manner as the right foot.

FIG. 16(1) illustrates a situation in which the user to be measured of the limb visually recognizes the instruction that "Please perform the first measurement motion related to the lower limb" displayed on the screen of the mobile terminal 160. FIG. 16(2) illustrates a state in which the user according to the instruction displayed on the screen of the mobile terminal 160 is stationary in preparation for the first measurement motion related to the lower limb. FIG. 16(3) illustrates a state in which the user performs a rotation motion around the hip joint as the first measurement motion. FIG. 16(4) illustrates a situation in which the user who has completed the first measurement motion related to the lower limb visually recognizes the instruction that "Please perform the second measurement motion related to the lower limb" displayed on the screen of the mobile terminal 160. FIG. 16(5) illustrates a state in which the user according to the instruction displayed on the screen of the mobile terminal 160 is seated on a chair in preparation for the second measurement motion related to the lower limb. FIG. 16(6) illustrates a state in which the user performs a rotation motion around the knee joint as the second measurement motion.

Figure 17:
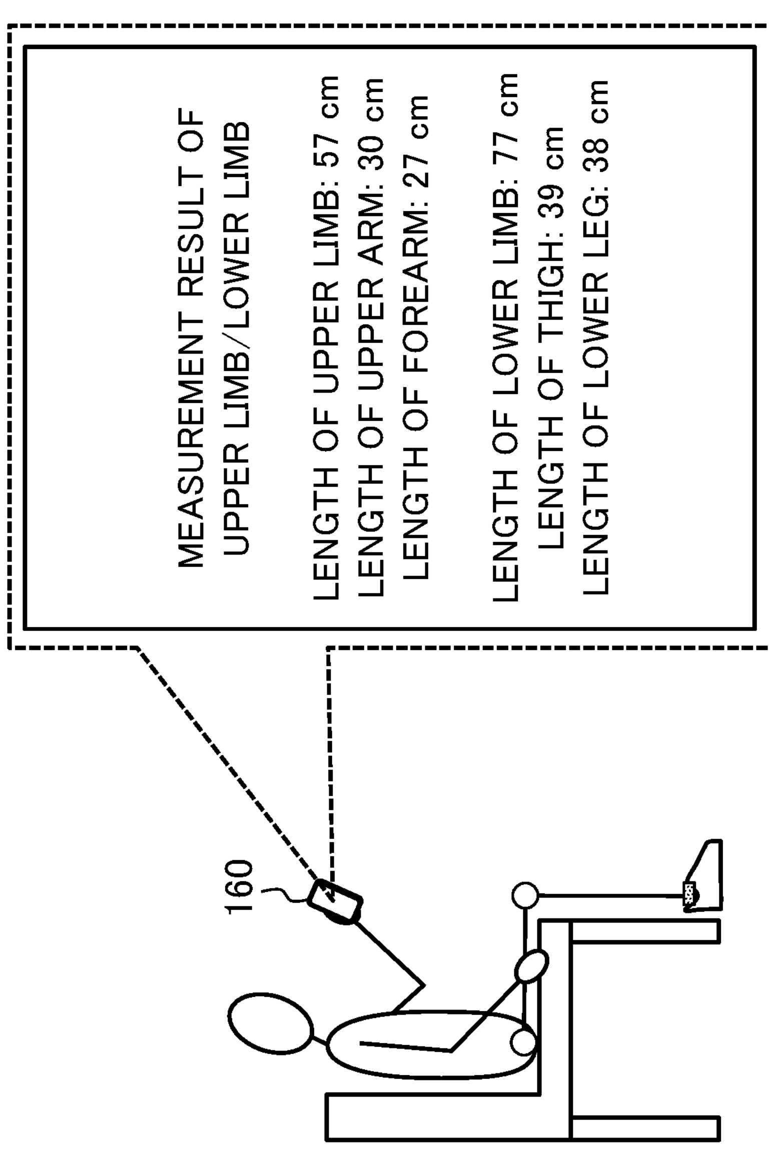
FIG. 17 is a conceptual diagram illustrating a display example of a measurement result of the upper limb/lower limb in the first application example according to the first example embodiment.

FIG. 17 illustrates a situation in which the user who has completed the measurement regarding the limb (upper limb/lower limb) visually recognizes the measurement result displayed on the screen of the mobile terminal 160. The user can confirm the length of his/her upper limb/lower limb by visually recognizing the measurement result displayed on the screen of the mobile terminal 160.

As described above, the measurement system of the present example embodiment includes at least one data acquisition device and a measurement device. The data acquisition device includes a sensor that measures a spatial acceleration and a spatial angular velocity. The data acquisition device is attached to a predetermined attachment site of the user. The data acquisition device is attached to a predetermined attachment site (wrist/ankle) of the user. The data acquisition device generates sensor data based on the spatial acceleration and the spatial angular velocity measured by the sensor according to the measurement motion related to the limb (upper limb/lower limb) of the user. The data acquisition device outputs the generated sensor data to the measurement device. The measurement device includes an acquisition unit, a calculation unit, an estimation unit, and an output unit. The acquisition unit acquires sensor data measured according to a measurement motion related to limb (upper limb/lower limb) of the user. The calculation unit calculates the length and the central angle of the arc related to the trajectory of the sensor in the period of the measurement motion using the sensor data measured by the sensor according to the measurement motion regarding the limb (upper limb/lower limb) of the user, the sensor being attached to the user at a predetermined attachment site. The estimation unit estimates the radius of the arc calculated using the calculated length and the calculated central angle as the length of the limb (upper limb/lower limb) of the user. The output unit outputs information about the length of the limb (upper limb/lower limb) of the user estimated by the estimation unit.

The measurement system of the present example embodiment focuses on the rotation motion of the limb (upper limb/lower limb) and estimates the length of the limb (upper limb/lower limb) based on the arc and the central angle of the trajectory of the sensor in the period of the measurement motion of the user. In the method of the present example embodiment, it is not necessary to strictly determine the start point and the end point of the measurement motion by the user, and it is only required to calculate the trajectory of the sensor. That is, in the method of the present example embodiment, strict restriction is not imposed on the user's motion. Therefore, according to the measurement system of the present example embodiment, it is possible to perform measurement regarding the limb based on sensor data measured according to a simple motion.

In an aspect of the present example embodiment, the calculation unit divides the trajectory of the sensor in the period of the measurement motion into a plurality of sections. The estimation unit calculates the radius of curvature of each divided section. The estimation unit estimates the length of the limb based on the distribution of the radii of curvature calculated for the plurality of sections. According to the present aspect, even when the trajectory of the sensor does not draw a clear arc, each of the divided sections is regarded as an arc, and the length of the limb can be estimated based on the distribution of the radii of curvature of the arcs.

In an aspect of the present example embodiment, the calculation unit calculates the length and the central angle of the first arc related to the trajectory of the sensor in the period of the first measurement motion according to the first measurement motion around the large joint (shoulder joint/hip joint). The calculation unit calculates the length and the central angle of the first arc using the sensor data in the period of the first measurement motion measured by the sensor attached to the portion of the small joint (wrist joint/ankle joint). The estimation unit calculates the radius of the first arc using the length and the central angle of the first arc calculated according to the first measurement motion. The estimation unit estimates the calculated radius of the first arc as the length of the limb (upper limb/lower limb). The calculation unit calculates the length and the central angle of the second arc related to the trajectory of the sensor in the period of the second measurement motion according to the second measurement motion around the middle joint (elbow joint/knee joint). The calculation unit calculates the length and the central angle of the second arc using the sensor data in the period of the second measurement motion measured by the sensor attached to the portion of the small joint (wrist joint/ankle joint). The estimation unit calculates the radius of the second arc using the length and the central angle of the second arc calculated according to the second measurement motion. The estimation unit estimates the calculated radius of the second arc as the length of the lower part (forearm/lower leg) of the limb. The estimation unit calculates the length of the upper part (upper arm/thigh) of the limb by subtracting the length of the lower part (forearm/lower leg) of the limb from the length of the limb (upper limb/lower limb).

In the present aspect, the measurement regarding the limb is performed using the sensor data in the period of the first measurement motion around the large joint (shoulder joint/hip joint) and the period of the second measurement motion around the middle joint (elbow joint/knee joint). According to the present aspect, the sensor is attached to the portion of the small joint (wrist joint/ankle joint), and the first measurement motion and the second measurement motion are performed, whereby the measurement regarding the limb (upper limb/lower limb) can be performed.

In an aspect of the present example embodiment, the limb is an upper limb, the large joint is a shoulder joint, the middle joint is an elbow joint, the small joint is a wrist joint, the upper part of the limb is an upper arm, and the lower part of the limb is a forearm. According to the present aspect, measurement regarding the upper limb can be performed.

In an aspect of the present example embodiment, the limb is a lower limb, the large joint is a hip joint, the middle joint is a knee joint, the small joint is an ankle joint, the upper part of the limb is a thigh, and the lower part of the limb is a lower leg. According to the present aspect, measurement regarding the lower limb can be performed.

In an aspect of the present example embodiment, the measurement device displays information instructing a measurement motion related to limb (upper limb/lower limb) on a screen of the terminal device at a position visually recognizable by the user. The measurement device estimates a length related to limb (upper limb/lower limb) of the user using sensor data measured by a data acquisition device attached to a predetermined attachment site of the user who has performed the measurement motion according to the instruction displayed on the screen of the terminal device. The measurement device displays the estimated length information about the limb of the user on the screen of the terminal device. According to the present aspect, it is possible to perform the measurement regarding the limb (upper limb/lower limb) by performing the measurement motion according to the instruction displayed on the screen of the terminal device. Furthermore, according to the present aspect, information including the measured length of the limb (upper limb/lower limb) can be confirmed on the screen of the terminal device.

Second Example Embodiment

Next, a measurement system according to a second example embodiment will be described with reference to the drawings. The information processing system of the present example embodiment measures the length of the limb (upper limb/lower limb) of the user using the sensor data measured by the sensor when the user performs a specific motion (also referred to as a measurement motion) with the sensor attached to a predetermined attachment site. In the present example embodiment, the predetermined attachment sites are a position of a wrist or an ankle corresponding to a position of a small joint (wrist joint/ankle joint) and a position of an elbow or a knee corresponding to a position of a middle joint (elbow joint/knee joint). The measurement system of the present example embodiment performs measurement related to the limb (upper limb/lower limb) using sensor data measured in a state where the sensor is attached to the positions of the small joints (wrist joints/ankle joints) and the middle joint (elbow joint/knee joint).

(Configuration)

Figure 18:
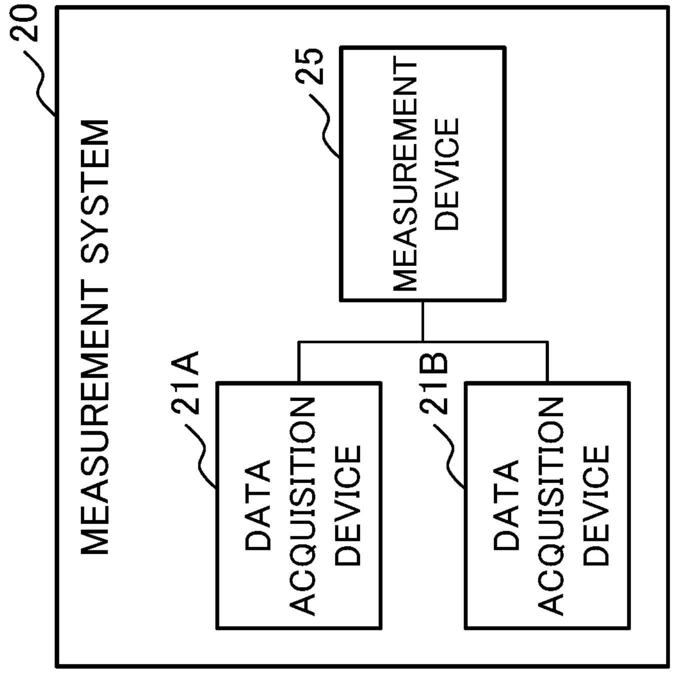
FIG. 18 is a block diagram illustrating an example of a configuration of a measurement system according to a second example embodiment.

FIG. 18 is a block diagram illustrating an example of a configuration of a measurement system 20 of the present example embodiment. The measurement system 20 includes a data acquisition device 21A, a data acquisition device 21B, and a measurement device 25. Each of the data acquisition device 21A and the data acquisition device 21B and the measurement device 25 may be connected by wire or wirelessly. Each of the data acquisition device 21A and the data acquisition device 21B and the measurement device 25 may be configured by a single device. The measurement system 20 may be configured only by the measurement device 25 by excluding the data acquisition device 21A and the data acquisition device 21B from the configuration of the measurement system 20.

The data acquisition device 21A and the data acquisition device 21B have the same configurations as the data acquisition device 11 of the first example embodiment. The data acquisition device 21A and the data acquisition device 21B are installed on a predetermined attachment site (wrist, ankle, elbow, knee) of a person such as a user or a subject. In the present example embodiment, the data acquisition device 21A is attached at a position of a wrist or an ankle corresponding to a position of a small joint (wrist joint/ankle joint). The data acquisition device 21B is attached at a position of an elbow or a knee corresponding to a position of a middle joint (elbow joint/knee joint). In the present example embodiment, a portion of a wrist or an ankle is referred to as a first attachment site, and a portion of an elbow or a knee is referred to as a second attachment site. That is, the data acquisition device 21A is attached to the first attachment site, and the data acquisition device 21B is attached to the second attachment site.

Each of the data acquisition device 21A and the data acquisition device 21B includes a sensor that measures an acceleration and an angular velocity. The sensor included in the data acquisition device 21A may be referred to as a first sensor, and the sensor included in the data acquisition device 21B may be referred to as a second sensor. The data acquisition device 21A and the data acquisition device 21B measure accelerations in the three axial directions (also referred to as spatial accelerations) and angular velocities around the three axes (also referred to as spatial angular velocities) as physical quantities related to movement of the limb (upper limb/lower limb) of a person. The physical quantity related to the movement of the limb (upper limb/lower limb) measured by the data acquisition device 21A and the data acquisition device 21B also includes a speed and an angle calculated by integrating the acceleration and the angular velocity. The physical quantity related to the motion of the upper limb/lower limb measured by the data acquisition device 21A and the data acquisition device 21B also includes a position (trajectory) calculated by second-order integration of the acceleration. The data acquisition device 21A and the data acquisition device 21B convert the measured physical quantity into digital data (also referred to as sensor data). The data acquisition device 21A and the data acquisition device 21B transmit the converted sensor data to the measurement device 25.

In the present example embodiment, the motion related to the limb (upper limb/lower limb) is a measurement motion (also referred to as a first measurement motion) around the large joint (shoulder joint/hip joint). The first measurement motion is a rotation motion around a large joint (shoulder joint/hip joint). For example, the sensor data acquired by the data acquisition device 21A and the data acquisition device 21B according to the motion of the upper limb/lower limb includes an identification code.

The identification code is a code for identifying the attachment site (wrist/ankle) of the data acquisition device 21A and the attachment site (elbow/knee) of the data acquisition device 21B. For example, the sensor data includes an identification code indicating which of the data acquisition device 21A and the data acquisition device 21B has measured the sensor data. For example, the sensor data includes an identification code indicating that the data was acquired by the data acquisition device 21A attached to which first attachment site (wrist/ankle) in left or right. For example, the sensor data includes an identification code indicating that the data was acquired by the data acquisition device 21B attached to which second attachment site (elbow/knee) in left or right. The format of the sensor data including the identification code is not particularly limited.

As in the first example embodiment, the measurement device 25 includes an acquisition unit, a calculation unit, an estimation unit, and an output unit (the drawings are omitted). The measurement device 25 acquires sensor data from the data acquisition device 21A and the data acquisition device 21B. The measurement device 25 measures the length of the limb (upper limb/lower limb) using the acquired sensor data. The measurement device 25 estimates the length of the limb (upper limb/lower limb) using sensor data measured according to a measurement motion related to the limb (upper limb/lower limb). For example, the measurement device 25 performs second-order integration on the spatial acceleration included in the sensor data measured according to the measurement motion to calculate the spatial position (trajectory). For example, the measurement device 25 calculates the spatial angle by integrating the spatial angle included in the sensor data measured according to the measurement motion. The measurement device 25 calculates the radii of rotation of the data acquisition device 21A and the data acquisition device 21B during the measurement motion based on the calculated spatial position (trajectory) and calculated spatial angle. The radius of rotation of the data acquisition device 21A during the measurement motion corresponds to the length of the limb (upper limb/lower limb). The radius of rotation of the data acquisition device 21B during the measurement motion corresponds to the length of the upper part (upper arm/thigh) of the limb. The measurement device 25 calculates the length of the lower part (forearm/lower leg) of the limb by subtracting the length of the upper part (upper arm/thigh) of the limb from the length of the limb (upper limb/lower limb).

Figure 19:
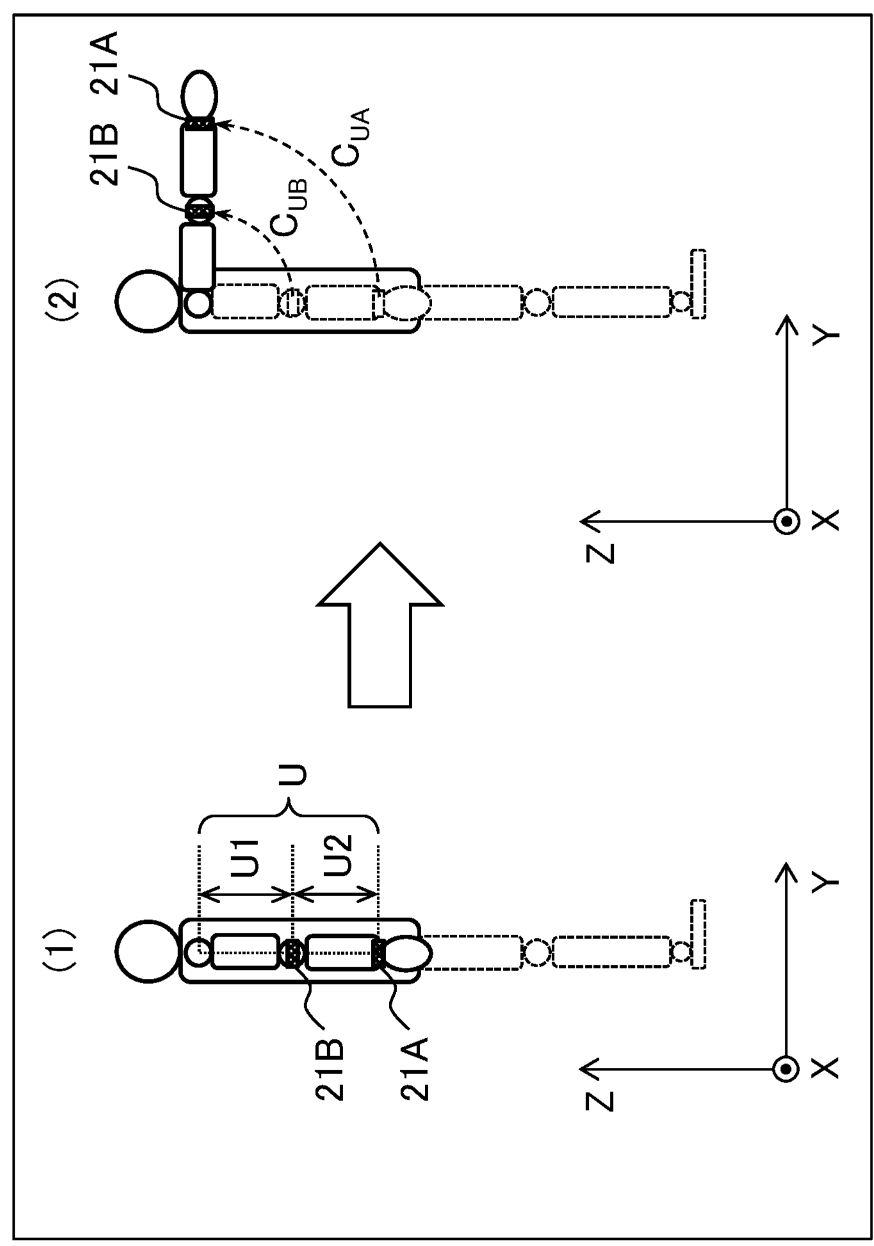
FIG. 19 is a conceptual diagram for describing an example of a measurement motion of the upper limb according to the second example embodiment.

FIG. 19 is a conceptual diagram for describing a measurement motion (first measurement motion) related to the upper limb. The data acquisition device 21A is attached to the wrist of the user to be measured. The data acquisition device 21B is attached to the elbow of the user to be measured. The length from the shoulder joint to the elbow joint (upper arm length) is U1. The length from the elbow joint to the wrist joint (length of the forearm) is U2. The sum of the length U1 of the upper arm and the length U2 of the forearm corresponds to the length U of the upper limb.

FIG. 19(1) is a preparation stage of the measurement motion regarding the upper limb. In FIG. 19(1), the user stands upright with the hand facing downward (−Z direction) with the upper limb straightly extended. FIG. 19(2) illustrates a state in which the user is performing the measurement motion. The measurement motion related to the upper limb is a motion of rotating the upper limb around the shoulder joint in a state where the elbow joint is straight. In the example of FIG. 19, the user rotates the upper limb on the YZ plane (sagittal plane). The measurement device 25 calculates trajectories of the data acquisition device 21A and the data acquisition device 21B at the time of transition from the state of FIG. 19(1) to the state of FIG. 19(2).

In the present example embodiment, the measurement motion related to the upper limb includes a circular motion around the shoulder joint based on the trajectory of the data acquisition device 21A and a circular motion around the shoulder joint based on the trajectory of the data acquisition device 21B. The circular motion around the shoulder joint based on the trajectory of the data acquisition device 21A draws an arc $C_{UA}$ (also referred to as a first arc). The circular motion around the shoulder joint based on the trajectory of the data acquisition device 21B draws an arc $C_{UB}$ (also referred to as a third arc). The measurement motion related to the upper limb is not limited to be performed on be performed on the YZ plane (sagittal plane), but may be performed on the XY plane (horizontal plane) or the ZX plane (coronal plane). The first measurement motion regarding the upper limb may include a mixture of motions on the YZ plane (sagittal plane), the XY plane (horizontal plane), and the ZX plane (coronal plane). When the measurement motion related to the upper limb is not limited to be performed on the single plane, the three-dimensional trajectories of the data acquisition device 21A and the data acquisition device 21B may be calculated. FIG. 19 illustrates an example of transition from the state of FIG. 19(1) to the state of FIG. 19(2). As long as the rotation motion around the shoulder joint is performed with the upper limb straightly extended, the positions of the start point and the end point of the measurement motion related to the upper limb are not particularly limited. For example, the upper limb may be reciprocated along a similar track. When the upper limb is reciprocated several times, the measurement accuracy regarding the length of the upper limb is improved by averaging the trajectories of the data acquisition device 21A and the data acquisition device 21B. The upper limb may be three-dimensionally rotated in different planes. When the upper limb is three-dimensionally rotated, the trajectories of the data acquisition device 21A and the data acquisition device 21B may be regarded as a spherical surface.

The measurement device 25 measures the length U of the upper limb based on the trajectory (arc $C_{UA}$) of the data acquisition device 21A. The measurement device 25 measures the length U1 of the upper arm based on the trajectory (arc $C_{UB}$) of the data acquisition device 21B. A method of calculating the length U of the upper limb and the length U1 of the upper arm is similar to that in the first example embodiment. The measurement device 25 calculates the length U2 of the forearm by subtracting the length U1 of the upper arm from the length U of the upper limb.

Figure 20:
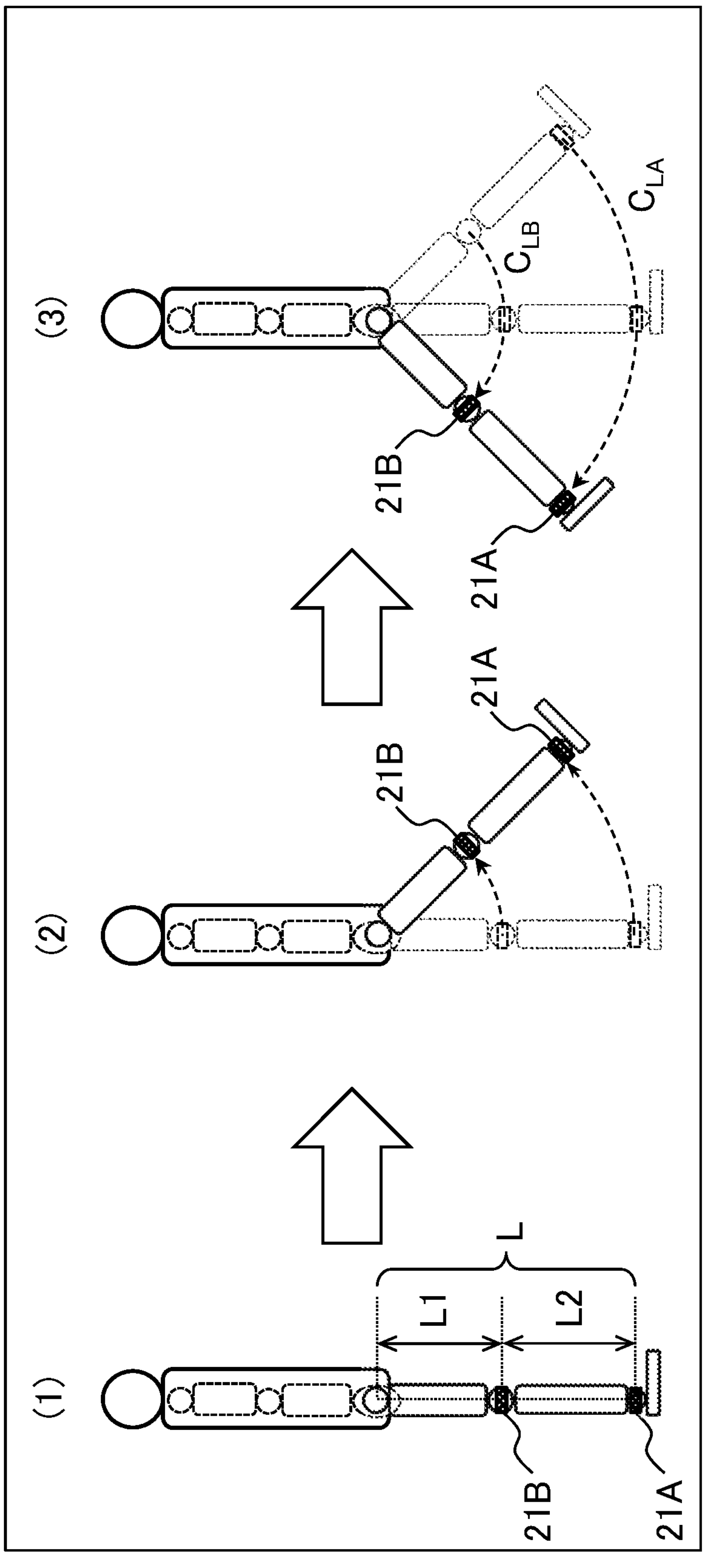
FIG. 20 is a conceptual diagram for describing an example of a measurement motion of the lower limb according to a second example embodiment.

FIG. 20 is a conceptual diagram for describing a measurement motion (first measurement motion) related to a lower limb. The data acquisition device 21A is attached to the ankle of the user to be measured. The data acquisition device 21B is attached to the knee of the user to be measured. The length from the hip joint to the knee joint (the length of the thigh) is L1. The length from the knee joint to the ankle joint (lower leg length) is L2. The sum of the length L1 of the thigh and the length L2 of the lower leg corresponds to the length L of the lower limb.

FIG. 20(1) illustrates a preparation stage of the measurement motion related to the lower limb. In FIG. 20(1), the user stands upright with the lower limb straightly extended. FIGS. 20(2) and 20(3) illustrate a state in which the user is performing the measurement motion. FIG. 20(2) illustrates a state in which the right foot kicks forward (+Y direction). FIG. 20(3) illustrates a state in which the right foot kicking forward (+Y direction) is pulled backward (−X direction). The measurement motion related to the lower limb is a motion of rotating the lower limb around the hip joint in a state where the knee joint is straight. In the example of FIG. 20, the user rotates the lower limb on the YZ plane (sagittal plane). The measurement device 25 calculates trajectories of the data acquisition device 21A and the data acquisition device 21B at the time of transition from the state of FIG. 20(1) to the state of FIG. 20(2) and then to the state of FIG. 20(3).

In the present example embodiment, the measurement motion related to the lower limb includes a circular motion around the hip joint based on the trajectory of the data acquisition device 21A and a circular motion around the hip joint based on the trajectory of the data acquisition device 21B. The circular motion around the hip joint based on the trajectory of the data acquisition device 21A draws an arc $C_{LB}$ (also referred to as a first arc). The circular motion around the hip joint based on the trajectory of the data acquisition device 21B draws an arc $C_{LA}$ (also referred to as a third arc). The measurement motion related to the lower limb is not limited to be performed on the YZ plane (sagittal plane), but may be performed on the XY plane (horizontal plane) or the ZX plane (coronal plane). The measurement motion related to the lower limb may include a mixture of motions on a YZ plane (sagittal plane), an XY plane (horizontal plane), and a ZX plane (coronal plane). In a case where the measurement motion related to the lower limb is not limited to be performed on a single plane, three-dimensional trajectories of the data acquisition device 21A and the data acquisition device 21B may be calculated. FIG. 20 illustrates an example of transition from the state of FIG. 20(1) to the state of FIG. 20(2) and then to the state of FIG. 20(3). As long as the rotation motion around the hip joint is performed with the lower limb straightly extended, the positions of the start point and the end point of the measurement motion related to the lower limb are not particularly limited. For example, the lower limb may be reciprocated along a similar track. When the lower limb is reciprocated several times, the measurement accuracy regarding the length of the lower limb is improved by averaging the trajectories of the data acquisition device 21A and the data acquisition device 21B. The lower limb may be three-dimensionally rotated in different planes. When the lower limb is three-dimensionally rotated, the trajectories of the data acquisition device 21A and the data acquisition device 21B may be regarded as a spherical surface.

The measurement device 25 measures the length L of the lower limb based on the trajectory (arc $C_{LA}$) of the data acquisition device 21A. The measurement device 25 measures the length L1 of the thigh based on the trajectory (arc $C_{LB}$) of the data acquisition device 21B. A method of calculating the length L of the lower limb and the length L1 of the thigh is similar to that in the first example embodiment. The measurement device 25 calculates the length L2 of the lower leg by subtracting the length L1 of the thigh from the length L of the lower limb.

The measurement device 25 outputs the calculated the measurement value regarding the limb (upper limb/lower limb). For example, the measurement device 25 outputs a measurement value regarding the limb (upper limb/lower limb) to a display device (not illustrated). For example, the measurement value regarding the limb (upper limb/lower limb) output to the display device is displayed on the screen of the display device. For example, the measurement device 25 outputs a measurement value regarding the limb (upper limb/lower limb) to an external system. For example, the measurement value regarding the limb (upper limb/lower limb) output to the external system is used for any application.

(Operation)

Next, an example of an operation of the measurement system 20 of the present example embodiment will be described with reference to the drawings. An example of the operation of the measurement device 25 of the measurement system 20 will be described with reference to a flowchart. The measurement motion regarding the upper limb and the measurement motion regarding the lower limb will be separately described. In the following, an example in which the measurement regarding the upper limb and the measurement regarding the lower limb is separately performed will be described, but the measurement regarding the upper limb and the measurement regarding the lower limb may be performed in the same flow.

[Measurement of Upper Limb]

FIG. 21 is a flowchart for describing an example of the operation of the measurement device 25 in the measurement related to the upper limb. In the description along the flowchart of FIG. 21, the measurement device 25 will be described as an operation subject.

In FIG. 21, first, the measurement device 25 acquires sensor data measured according to the measurement motion (first measurement motion) of the upper limb from the data acquisition device 21A and the data acquisition device 21B (step S211).

Next, the measurement device 25 calculates the spatial trajectory/spatial angle using the acquired sensor data (step S212).

Next, the measurement device 25 calculates the length of the upper limb using the spatial trajectory/spatial angle based on the measurement motion measured by the data acquisition device 21A attached to the wrist (step S213).

Next, the measurement device 25 calculates the length of the upper arm using the spatial trajectory/spatial angle based on the measurement motion measured by the data acquisition device 21B attached to the elbow (step S214). The order of the processing of step S213 and step S214 may be switched.

Next, the measurement device 25 calculates the length of the forearm by subtracting the length of the upper arm from the length of the upper limb (step S215).

Next, the measurement device 25 outputs the calculated values of the lengths of the upper limbs, the upper arm, and the forearm (also referred to as measurement values regarding the upper limb) (step S216). The measurement values regarding the upper limb output from the measurement device 25 is used according to the application.

[Measurement of Lower Limb]

Figure 22:
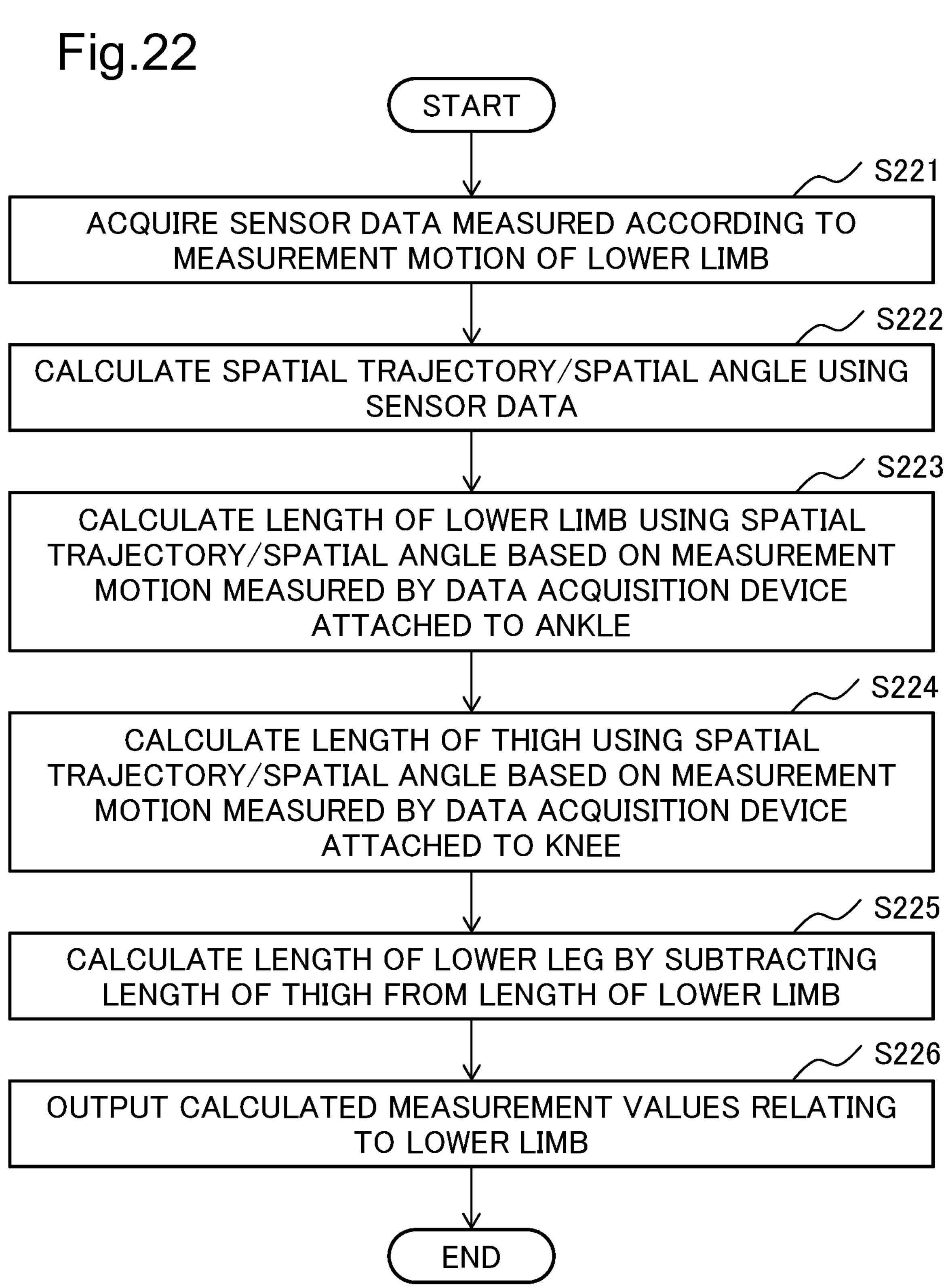
FIG. 22 is a flowchart for describing an example of measurement of the length of the lower limb by the measurement device of the measurement system according to the second example embodiment.

FIG. 22 is a flowchart for describing an example of the operation of the measurement device 25 in the measurement regarding the lower limb. In the description along the flowchart of FIG. 22, the measurement device 25 will be described as an operation subject.

In FIG. 22, first, the measurement device 25 acquires sensor data measured according to the measurement motion of the lower limb from the data acquisition device 21A and the data acquisition device 21B (step S221).

Next, the measurement device 25 calculates the spatial trajectory/spatial angle using the acquired sensor data (step S222).

Next, the measurement device 25 calculates the length of the lower limb using the spatial trajectory/spatial angle based on the measurement motion measured by the data acquisition device 21A attached to the ankle (step S223).

Next, the measurement device 25 calculates the length of the thigh using the spatial trajectory/spatial angle based on the measurement motion measured by the data acquisition device 21B attached to the knee (step S224). The order of the processing of step S223 and step S224 may be switched.

Next, the measurement device 25 calculates the lower leg length by subtracting the thigh length from the lower limb length (step S225).

Next, the measurement device 25 outputs the calculated values of the lengths of the lower limbs, the thigh, and the lower leg (also referred to as measurement values regarding the lower limb) (step S226). The measurement values regarding the lower limb output from the measurement device 25 is used according to the application.

Second Application Example

Next, the second application example according to the present example embodiment will be described with reference to the drawings. In the present application example, it is assumed that a user performs a measurement motion according to an instruction displayed on a display unit of a mobile terminal in which an application (also referred to as an "appli") having a function of the measurement device of the present example embodiment is installed. In the present application example, a mobile terminal is used, but any terminal device can be used as long as the screen can be disposed at a position visually recognizable by the user.

Figure 23:
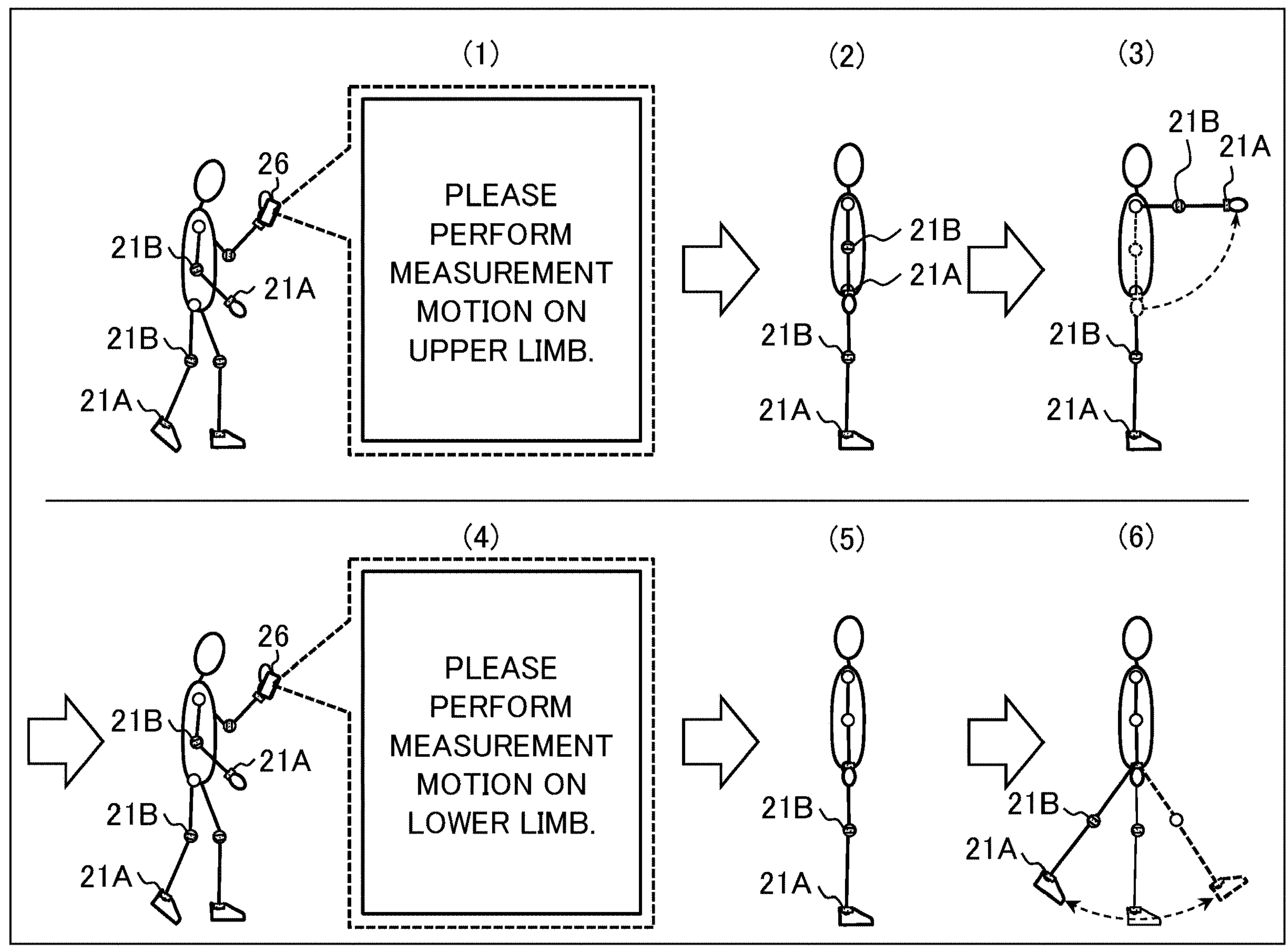
FIG. 23 is a conceptual diagram for describing measurement regarding the upper limb/lower limb in the second application example according to the second example embodiment.

FIG. 23 is a conceptual diagram for describing measurement related to limb (upper limb/lower limb). In the example of FIG. 23, the user wears the data acquisition device 21A (also referred to as a first sensor) on the wrist and the ankle, and wears the data acquisition device 21B (also referred to as a second sensor) on the elbow and the knee. For example, an instruction to wear the data acquisition device 21A on the wrist and the ankle and an instruction to wear the data acquisition device 21B on the elbow and the knee may be displayed on the screen of the mobile terminal 260. The user performs the measurement motion related to the upper limb/lower limb according to the instruction displayed on the screen of a mobile terminal 260. In the example of FIG. 23, an example of the measurement motion of the right hand and the right foot is illustrated. The measurement motions of the left hand and the left foot can also be performed in the same manner as the measurement motion of the right hand and the right foot.

FIG. 23(1) illustrates a situation in which the user to be measured of the limb visually recognizes the instruction that "Please perform the measurement motion related to the upper limb" displayed on the screen of the mobile terminal 260. FIG. 23(2) illustrates a state in which the user according to the instruction displayed on the screen of the mobile terminal 260 is stationary in preparation for the measurement motion related to the upper limb. FIG. 23(3) illustrates a state in which the user performs a rotation motion around the shoulder joint as the measurement motion related to the upper limb. FIG. 23(4) illustrates a situation in which the user who has completed the measurement motion related to the upper limb visually recognizes the instruction that "Please perform the measurement motion related to the lower limb" displayed on the screen of the mobile terminal 260. FIG. 23(5) illustrates a state in which the user in response to the instruction displayed on the screen of the mobile terminal 260 is stationary in preparation for the measurement motion related to the lower limb. FIG. 23(6) illustrates a state in which the user performs a rotation motion around the hip joint as a measurement motion related to the lower limb.

Figure 24:
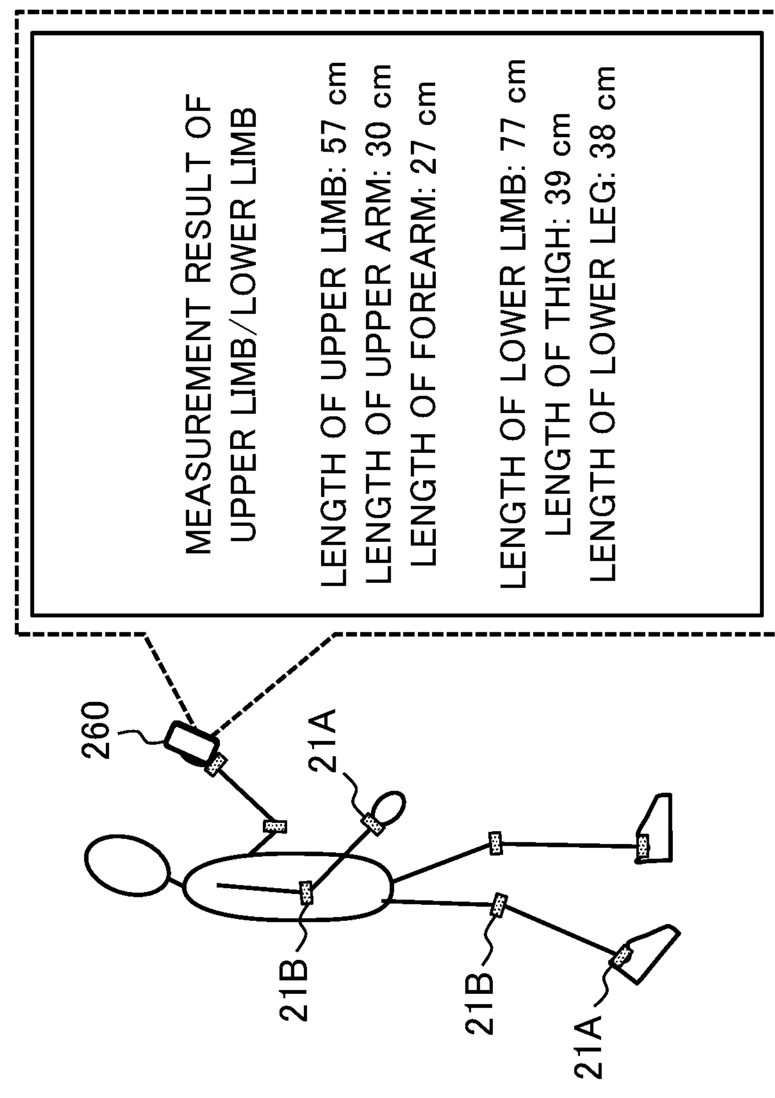
FIG. 24 is a conceptual diagram illustrating a display example of a measurement result of the upper limb/lower limb in the second application example according to the second example embodiment.

FIG. 24 illustrates a situation in which the user who has completed the measurement regarding the limb (upper limb/lower limb) visually recognizes the measurement result displayed on the screen of the mobile terminal 260. The user can confirm the length of his/her upper limb/lower limb by visually recognizing the measurement result displayed on the screen of the mobile terminal 260.

As described above, in the present example embodiment, the calculation unit calculates the length and the central angle of the first arc related to the trajectory of the first sensor in the period of the first measurement motion according to the first measurement motion around the large joint (shoulder joint/hip joint). The calculation unit calculates the length and the central angle of the first arc using the sensor data in the period of the first measurement motion measured by the first sensor attached to the portion of the small joint (wrist joint/ankle joint). The estimation unit calculates the radius of the first arc using the length and the central angle of the first arc calculated according to the first measurement motion. The estimation unit estimates the calculated radius of the first arc as the length of the limb (upper limb/lower limb). The calculation unit calculates the length and the central angle of the third arc related to the trajectory of the second sensor in the period of the first measurement motion using the sensor data measured by the second sensor attached to the portion of the middle joint (elbow joint/knee joint) according to the first measurement motion. The estimation unit calculates the radius of the third arc using the length and the central angle of the third arc calculated according to the first measurement motion. The estimation unit estimates the calculated radius of the third arc as the length of the upper part (upper arm/thigh) of the limb. The estimation unit calculates the length of the lower part (forearm/lower leg) of the limb by subtracting the length of the upper part (upper arm/thigh) of the limb from the length of the limb (upper limb/lower limb).

In the present aspect, the measurement regarding the limb (upper limb/lower limb) is performed using the sensor data in the period of the first measurement motion around the large joint (shoulder joint/hip joint). According to the present aspect, the sensor is attached to the portion of the small joint (wrist joint/ankle joint) and the middle joint (elbow joint/knee joint), and the first measurement motion is performed, whereby the measurement regarding the limb (upper limb/lower limb) can be performed at once.

Third Example Embodiment

Figure 25:
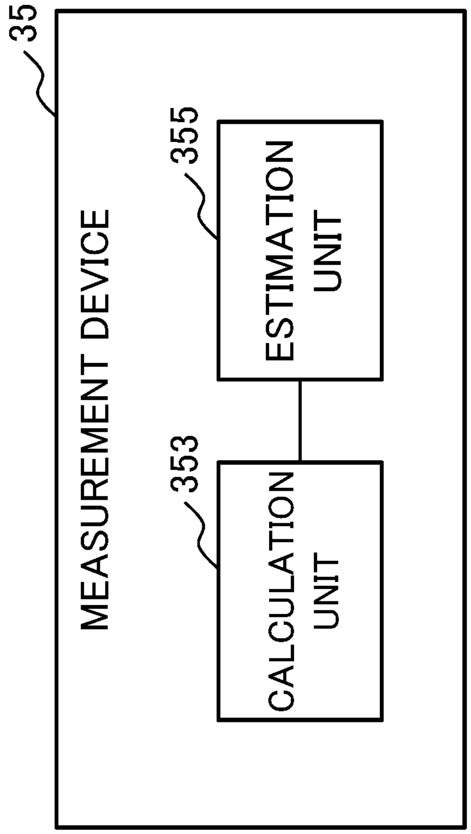
FIG. 25 is a block diagram illustrating an example of a configuration of a measurement device according to a third example embodiment.

Next, the measurement device according to a third example embodiment will be described with reference to the drawings. The measurement device of the present example embodiment has a configuration in which the measurement devices of the first and second example embodiments are simplified. FIG. 25 is a block diagram illustrating an example of a configuration of a measurement device 35 of the present example embodiment. The measurement device 35 includes a calculation unit 353 and an estimation unit 355.

The calculation unit 353 calculates the length of the arc and the central angle of the arc related to the trajectory of the sensor in the period of the measurement motion according to the measurement motion regarding the limb of the user, the sensor being attached to the user at a predetermined attachment site. Using the sensor data measured by the sensor, the calculation unit 353 calculates the length of the arc and the central angle of the arc related to the trajectory of the sensor in the period of the measurement motion period. The estimation unit 355 estimates the radius of the arc calculated using the length and the central angle of the arc calculated by the calculation unit 353 as the length of the limb (upper limb/lower limb) of the user.

The measurement device of the present example embodiment focuses on the rotation motion of the limb (upper limb/lower limb) and estimates the length of the limb (upper limb/lower limb) based on the arc and the central angle of the trajectory of the sensor measured in the motion period of the user. In the method of the present example embodiment, it is not necessary to strictly determine the start point and the end point of the motion by the user, and it is only required to calculate the trajectory of the sensor. That is, in the method of the present example embodiment, strict restriction is not imposed on the user's motion. Therefore, according to the measurement device of the present example embodiment, it is possible to perform measurement regarding the limb (upper limb/lower limb) based on sensor data measured according to a simple motion.

(Hardware)

Regarding a hardware configuration that performs control and processing according to each example embodiment of the present disclosure, an information processing device 90 (computer) in FIG. 26 will be described as an example. The information processing device 90 in FIG. 26 is a configuration example for performing control and processing of each example embodiment, and does not limit the scope of the present disclosure.

Figure 26:
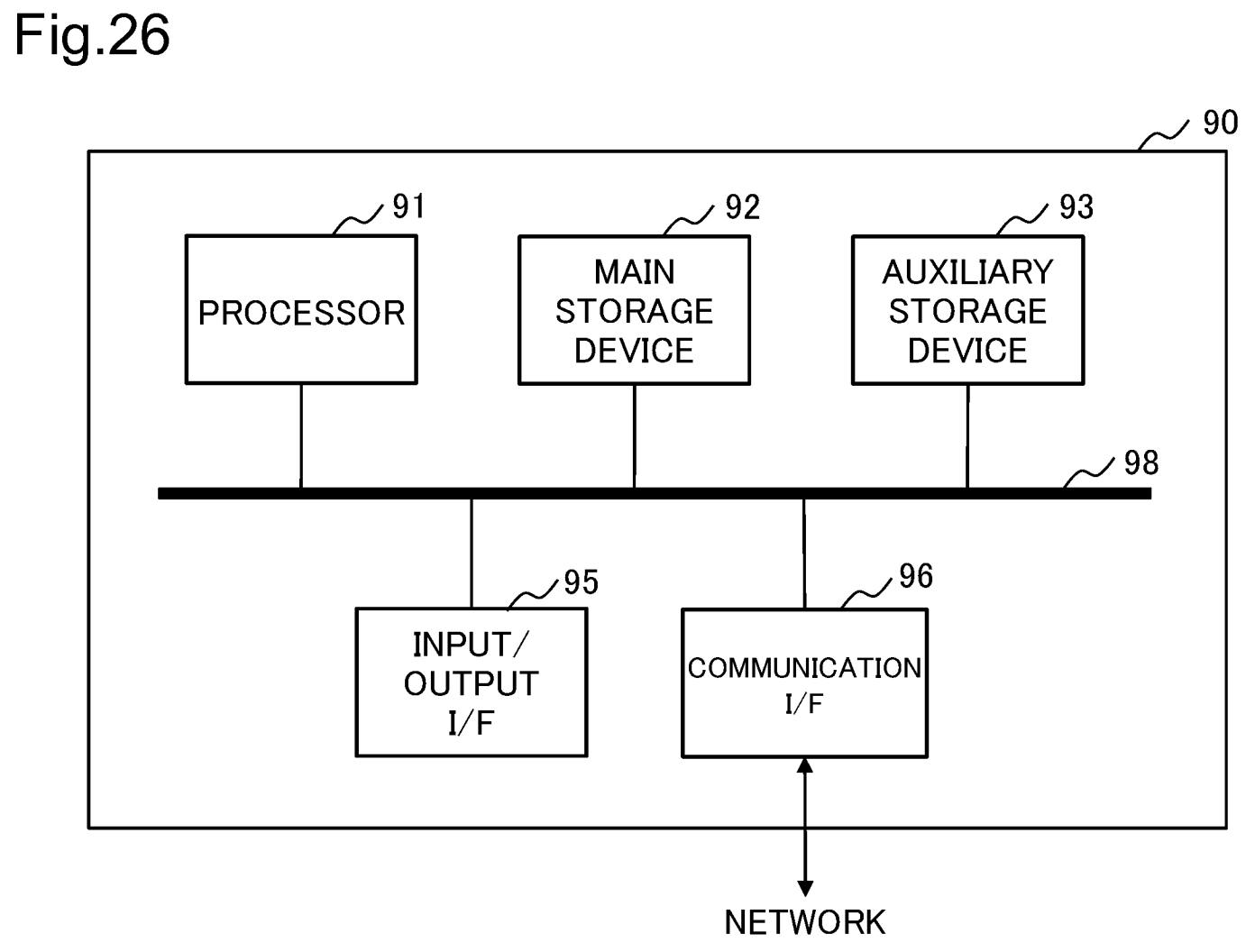

As illustrated in FIG. 26, the information processing device 90 includes a processor 91, a main storage device 92, an auxiliary storage device 93, an input/output interface 95, and a communication interface 96. In FIG. 26 the interface is abbreviated as an interface (I/F). The processor 91, the main storage device 92, the auxiliary storage device 93, the input/output interface 95, and the communication interface 96 are data-communicably connected to each other via a bus 98. The processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92. The processor 91 executes the program developed in the main storage device 92. In the present example embodiment, a software program installed in the information processing device 90 may be used. The processor 91 executes control and processing according to the present example embodiment.

The main storage device 92 has an area in which a program is developed. A program stored in the auxiliary storage device 93 or the like is developed in the main storage device 92 by the processor 91. The main storage device 92 is achieved by, for example, a volatile memory such as a dynamic random access memory (DRAM). A nonvolatile memory such as a magnetoresistive random access memory (MRAM) may be configured and added as the main storage device 92.

The auxiliary storage device 93 stores various pieces of data such as programs. The auxiliary storage device 93 is achieved by a local disk such as a hard disk or a flash memory. Various pieces of data may be stored in the main storage device 92, and the auxiliary storage device 93 may be omitted.

The input/output interface 95 is an interface that connects the information processing device 90 with a peripheral device based on a standard or a specification. The communication interface 96 is an interface that connects to an external system or a device through a network such as the Internet or an intranet in accordance with a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input of information and settings. In a case where the touch panel is used as the input device, the display screen of the display device may also serve as the interface of the input device. Data communication between the processor 91 and the input device may be mediated by the input/output interface 95.

The information processing device 90 may be provided with a display device that displays information. In a case where a display device is provided, the information processing device 90 preferably includes a display control device (not illustrated) that controls display of the display device. The display device may be connected to the information processing device 90 via the input/output interface 95.

The information processing device 90 may be provided with a drive device. The drive device mediates reading of data and a program from the recording medium, writing of a processing result of the information processing device 90 to the recording medium, and the like between the processor 91 and the recording medium (program recording medium). The drive device may be connected to the information processing device 90 via the input/output interface 95.

The above is an example of a hardware configuration for enabling control and processing according to each example embodiment of the present example invention. The hardware configuration of FIG. 26 is an example of a hardware configuration for executing control and processing according to each example embodiment, and does not limit the scope of the present example invention. A program for causing a computer to execute control and processing according to each example embodiment is also included in the scope of the present example invention. A program recording medium in which the program according to each example embodiment is recorded is also included in the scope of the present example invention. The recording medium can be achieved by, for example, an optical recording medium such as a compact disc (CD) or a digital versatile disc (DVD). The recording medium may be achieved by a semiconductor recording medium such as a Universal Serial Bus (USB) memory or a secure digital (SD) card. The recording medium may be achieved by a magnetic recording medium such as a flexible disk, or another recording medium. In a case where the program executed by the processor is recorded in the recording medium, the recording medium is a program recording medium.

The components included in the device of each example embodiment may be combined in any manner. The components included in the device of each example embodiment may be achieved by software or may be achieved by a circuit.

While the present example invention is described with reference to example embodiments thereof, the present example invention is not limited to these example embodiments. Various modifications that can be understood by those of ordinary skill can be made to the configuration and details of the present example invention within the scope of the present example invention.

This application claims priority based on Japanese Patent Application No. 2021-075661 filed on Apr. 28, 2021, the entire disclosure of which is incorporated herein.

REFERENCE SIGNS LIST

10, 20 measurement system
11, 21A, 21B data acquisition device
15, 25, 35 measurement device
111 acceleration sensor
112 angular velocity sensor
113 control unit
115 transmission unit
151 acquisition unit
153, 353 calculation unit
155, 355 estimation unit
157 output unit

What is claimed is:

1. A measurement device comprising:
a memory storing instructions; and
a processor connected to the memory and configured to execute the instructions to:
calculate, using sensor data measured by a sensor according to a measurement motion regarding a limb of a user, the sensor being attached to the user at a predetermined attachment site, a length and a central angle of an arc related to a trajectory of the sensor in a period of the measurement motion; and
estimate a radius of the arc calculated using the calculated length and the calculated central angle of the arc as a length of the limb of the user.

2. The measurement device according to claim 1, wherein the processor is configured to execute the instructions to divide a trajectory of the sensor in a period of the measurement motion into a plurality of sections,
calculate a radius of curvature for each of the divided sections, and
estimate the length of the limb based on a distribution of the radii of curvature calculated for the plurality of sections.

3. The measurement device according to claim 1, wherein the processor is configured to execute the instructions to
calculate, using sensor data measured by the sensor attached to a portion of a small joint according to a first measurement motion around a large joint, a length and a central angle of a first arc related to the trajectory of the sensor in a period of the first measurement motion,
calculate, using sensor data measured by the sensor attached to the portion of the small joint according to a second measurement motion around a middle joint, a length and a central angle of a second arc related to the trajectory of the sensor in a period of the second measurement motion,
calculate a radius of the first arc using the length and the central angle of the first arc calculated according to the first measurement motion,
estimate the calculated radius of the first arc as the length of the limb,
calculate a radius of the second arc using the length and the central angle of the second arc calculated according to the second measurement motion,
estimate the calculated radius of the second arc as a length of a lower part of the limb, and
calculate a length of an upper part of the limb by subtracting the length of the lower part of the limb from the length of the limb.

4. The measurement device according to claim 3, wherein the limb is an upper limb, the large joint is a shoulder joint, the middle joint is an elbow joint, the small joint is a wrist joint, the upper part of the limb is an upper arm, and the lower part of the limb is a forearm.

5. The measurement device according to claim 3, wherein the limb is a lower limb, the large joint is a hip joint, the middle joint is a knee joint, the small joint is an ankle joint, the upper part of the limb is a thigh, and the lower part of the limb is a lower leg.

6. A measurement method executed by a computer, the method comprising:
calculating, using sensor data measured by a sensor according to a measurement motion regarding a limb of a user, the sensor being attached to the user at a predetermined attachment site, a length and a central angle of an arc related to a trajectory of the sensor in a period of the measurement motion; and
estimating a radius of the arc calculated using the calculated length and the calculated central angle of the arc as a length of the limb of the user.

7. A non-transitory recording medium storing a program for causing a computer to execute:
calculating, using sensor data measured by a sensor according to a measurement motion regarding a limb of a user, the sensor being attached to the user at a predetermined attachment site, a length and a central angle of an arc related to a trajectory of the sensor in a period of the measurement motion; and
estimating a radius of the arc calculated using the calculated length and the calculated central angle of the arc as a length of the limb of the user.

* * * * *